(12) United States Patent
Tsabari et al.

(10) Patent No.: US 8,753,678 B2
(45) Date of Patent: *Jun. 17, 2014

(54) METHOD AND APPARATUS FOR FORMING DELIVERY DEVICES FOR ORAL INTAKE OF AN AGENT

(75) Inventors: Moshe Tsabari, Jerusalem (IL); Avner Balshey, Mevasseret Tsion (IL); Erez Yofe, Srigim (IL); Michael Friedman, Jerusalem (IL)

(73) Assignee: Intec Pharma Ltd., Jerusalem (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/613,718

(22) Filed: Sep. 13, 2012

(65) Prior Publication Data
US 2013/0101631 A1 Apr. 25, 2013

Related U.S. Application Data

(63) Continuation of application No. 12/087,888, filed as application No. PCT/IL2007/000070 on Jan. 18, 2007, now Pat. No. 8,298,574.

(60) Provisional application No. 60/759,554, filed on Jan. 18, 2006.

(51) Int. Cl.
*A61K 9/48* (2006.01)
*A61K 9/70* (2006.01)

(52) U.S. Cl.
USPC ............ 424/451; 424/409; 424/453; 424/457

(58) Field of Classification Search
USPC .................. 424/410, 443, 472, 457, 409, 451
See application file for complete search history.

(56) References Cited

U.S. PATENT DOCUMENTS

| | | | | |
|---|---|---|---|---|
| 2,901,951 | A | * | 9/1959 | Hochfeld ...................... 493/442 |
| 4,128,445 | A | * | 12/1978 | Sturzenegger et al. ......... 156/64 |
| 4,451,260 | A | | 5/1984 | Mitra |
| 5,472,710 | A | | 12/1995 | Klokkers-Bethke et al. |
| 6,669,954 | B2 | | 12/2003 | Crison et al. |
| 6,685,962 | B2 | * | 2/2004 | Friedman et al. ............. 424/457 |
| 6,911,217 | B1 | | 6/2005 | Gren et al. |

FOREIGN PATENT DOCUMENTS

| | | |
|---|---|---|
| EP | 0 090 560 A2 | 10/1983 |
| FR | 1.392.464 | 4/1963 |
| GB | 1 058 105 | 2/1967 |
| WO | 01/37812 A2 | 5/2001 |
| WO | 03/105812 A1 | 12/2003 |
| WO | 2005/009199 A2 | 2/2005 |

OTHER PUBLICATIONS

Klausner, et al., "Novel Gastroretentive Dosage Forms: Evaluation of Gastroretentivity and Its Effect on Levodopa Absorption in Humans", Pharmaceutical Research, vol. 20, No. 9, pp. 1466-1473, (2003).

Klausner, et al., "Novel levodopa gastroretentive dosage form: in-vivo evaluation in dogs", Journal of Controlled Release, vol. 88, pp. 117-126, (2003).

The International Search Report for International Application No. PCT/IL2007/000070, mailed Jul. 23, 2007, five pages.

U.S. Appl. No. 12/087,888.

* cited by examiner

*Primary Examiner* — Michael G Hartley
*Assistant Examiner* — Micah-Paul Young
(74) *Attorney, Agent, or Firm* — Vorys, Sater, Seymour and Pease LLP; Susanne M. Hopkins; William L. Klima

(57) ABSTRACT

Provided are methods, systems and apparatuses for producing delivery devices, for example, for oral intake of an agent. The method can include assembling one or more layers including one or more materials with an agent or an agent-releasing formulation to form an intergraded device; folding the intergrated delivery device to form a folded integrated delivery device; and at least partially enclosing the folded delivery device to a form suitable for oral delivery.

17 Claims, 16 Drawing Sheets

METHOD AND APPARATUS FOR FORMING DELIVERY DEVICES FOR ORAL INTAKE OF AN AGENT

FIELD OF THE INVENTION

This invention relates generally to methods and apparatuses for forming delivery systems for the controlled release of active agents and more preferably for forming delivery system with gastroretentivity.

BACKGROUND OF THE INVENTION

Many controlled release dosage forms have been developed for the delivery of pharmaceutical drugs for prolonging the release and absorption of the drug in the alimentary canal. Similarly, many methods and types of apparatus have been invented to produce such drugs. For example, U.S. Pat. No. 5,472,710 to Klokkers-Bethke et al., discloses a pharmaceutical preparation to be administered orally with controlled release of an active substance and a method for the manufacture of the preparation.

U.S. Pat. No. 6,669,954 to Crison et al., discloses devices for controlled release of drugs.

U.S. Pat. No. 6,685,962, to Friedman et al., discloses gastro-retentive controlled release pharmaceutical dosage forms.

U.S. Pat. No. 6,911,217 to Gren et al., discloses a controlled release bead, a method for producing the same and a multiple unit formulation comprising the bead.

WO 03/105812 A1 describes an extruded pharmaceutical product for retention in the stomach; comprising a sheet of hydratable polymer of a size that does not exit the stomach; a shaped sheet; a planar sheet that is rolled or folded or otherwise compacted; and a sealed hollow tubular extrudate.

WO 2005/009199 describes an automated process and apparatus for making a gastro retentive device, having a pouch assembly or capsule assembly.

Despite the numerous advances in the development of controlled release delivery formulations, there is a still a need to develop apparatus and methods for reliable mass production of agent delivery formulations.

SUMMARY OF THE INVENTION

The present invention provides, in accordance with a first of its aspects, a method for producing an agent delivery device for oral intake, the method comprising:
(i) assembling one or more layers comprising one or more materials with an agent or an agent-releasing formulation to form an intergraded device;
(ii) folding said integrated delivery device to form a folded integrated delivery device; and
(iii) at least partially enclosing said folded delivery device to a form suitable for oral delivery.

The delivery device may be a single layer device or a multi-layered device. The layers are preferably made of a polymeric composition, each layer comprising a single polymer or a combination of polymers, and the composition of polymers in one layer may be the same or different from that of other layers in the device. The layers may also be divided into compartments of the same or different constituents.

The invention also provides, in accordance with a second of its aspects, an agent delivery device for oral intake comprising a folded single or multi-layered integrated device comprising the agent or agent releasing formulation, the folded integrated device being at least partially enclosed within or by an enclosure, whenever the device is produced by the method of the invention. The oral delivery device serves as a platform for the delivery of any agent, the oral intake of which is required. The various applications will be dictated by the agent selected, the type of polymers selected, the type of enclosure etc, etc.

The agent, which as will be further described hereinbelow, may be for oral intake either for purposes of therapy (e.g. a drug), diagnostics (e.g. a contrasting agent), or for a subject's general health (e.g. a nutrient). It is preferable that the agent be releasable from the device.

Due to the characteristic features of the integrated device obtained in accordance with the invention, the release of the agent from the device, once wetted by gastric medium, is in a controlled, while being retained in the gastrointestinal tract.

The invention also provides, in accordance with a third aspect, a system for producing an agent-delivery device for oral intake, the system comprising:
(i) an assembly apparatus adapted to assemble one or more layers comprising one or more materials and an agent or an agent-releasing formulation to form an intergraded device comprising said agent or agent-releasing formulation;
(ii) a folding apparatus adapted to fold the integrated device into a folded integrated device; and
(iii) an enclosing apparatus adapted to at least partially enclose the folded integrated device within an enclosure to form a device in a form suitable for oral delivery.

It is to be noted that the invention also provides a folding apparatus per se, for folding a single or multi-layered sheet which may be the same or different from those defined herein. The folding apparatus, according to this aspect of the invention comprises a primary press with two opposite faces, each face having a corrugated surface with ridges of one corrugated surface being essentially opposite to troughs of the other corrugated surface and essentially fitting one into the other; whereby upon placing at least a portion of the single or multi-layered sheet in the press and pressing the two opposite faces one versus the other a three dimensional device having at least said portion undulated is formed with undulations that correspond in shape to that of said corrugated surfaces. The folding apparatus may comprise a secondary press comprising opposite faces perpendicular to the faces of said primary press and adapted to press the undulated device so as to form a more compacted folded device having a dimension which is preferably at least five times smaller than that of the sheet prior to pressing.

With respect to the folding apparatus there is thus also provided a method for folding a single or multi-layered sheet comprising:
(i) placing said single or multi-layered sheet in a folding apparatus in accordance with the invention;
(ii) pressing two opposite faces of the press one versus the other to form an undulated, three dimensional device with undulations that correspond in shape to that of said corrugated surfaces; and
(iii) optionally, pressing two opposite faces perpendicular to the direction of press applied in step (ii).

BRIEF DESCRIPTION OF THE DRAWINGS

In order to understand the invention and to see how it may be carried out in practice, a preferred embodiment will now be described, by way of non-limiting example only, with reference to the accompanying drawings, in which.

Figure 1A:
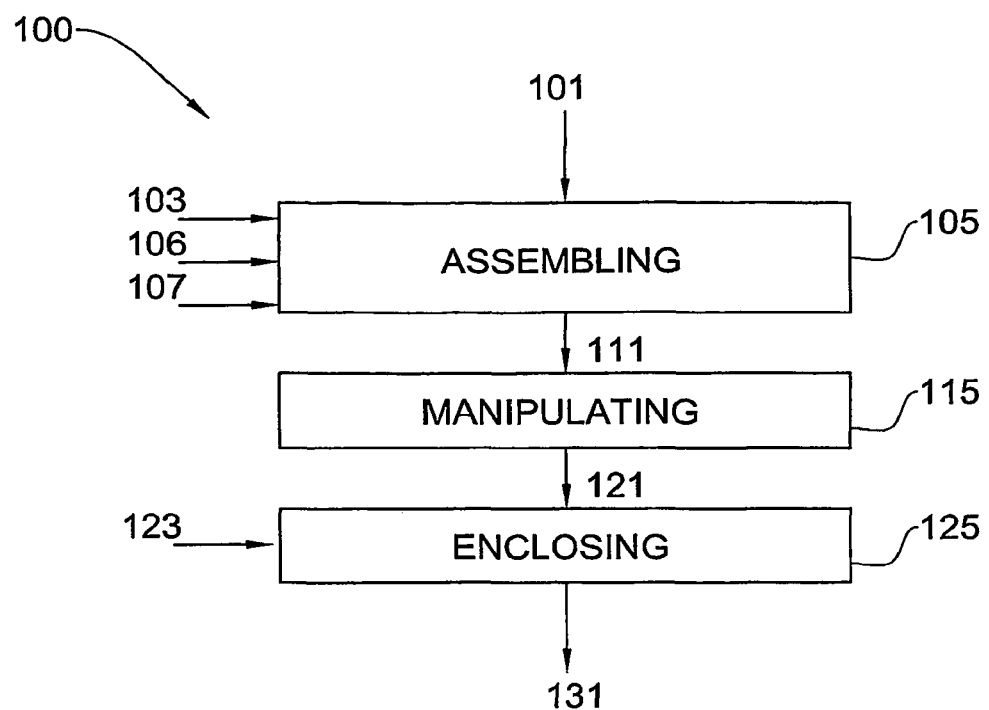
FIG. 1A is a simplified flowchart illustrating the major process steps of a method for producing a compacted agent delivery device in accordance with an embodiment of the present invention.

DETAILED DESCRIPTION OF THE INVENTION AND SOME NON-LIMITING EXEMPLARY EMBODIMENTS

The present invention is directed to methods and apparatuses for producing agent delivery devices for oral intake and particularly to compacted laminated gastro-retentive/controlled release dosage forms. The dosage forms typically comprise at least one active agent which is physically retained within or on at least one compartment (section) or layer of the device. The compartment may at least partially surround the agent, or entrap the agent or the agent may be embedded or adsorbed into a layer, as will be further discussed hereinbelow. Additionally or alternatively, the agent may be bound chemically to one or more compartments/layers of the device. The structure containing the agent may be further surrounded by an at least partially enclosing frame so as to form a generally planar assembly. Sometimes the assembly will have external layers affixed thereto so as to form a laminated device.

Glossary

In the following description and claims use will be made, at times, with a variety of terms, and the meaning of such terms as they should be construed in accordance with the invention is as follows:

By "an agent" is meant an entity, a substance or a chemical capable of producing an effect. The agent may be a pharmaceutical drug, a substance, such as a contrasting agent to be used for diagnostic or, a nutritional substance. As will be to appreciated the invention is not limited to any specific agent and generally it may be any agent that is administered orally for either systemic effect or a local effect within the gastrointestinal (GI) tract. The agent may be incorporated in the delivery device in its active form or in a pro-active form, e.g. as a pro-drug, such that only upon contact with body fluids (e.g. gastric content), it is converted to its active form.

By "an agent releasing formulation" is meant a formulation comprising the agent and at least one pharmaceutically acceptable carrier as well as formulations in which the agent is attached (physical or chemical attachment) to or in a nano- or microparticles, powder, liquid or compressed solids or to a matrix. The agent-releasing formulation may include other pharmaceutically acceptable excipients, as known to those versed in the pharmacy. In the following description the term agent and agent-releasing formulation may be used interchangeably to denote the agent either in a free form or as part of a formulation.

As used herein, "a drug" is meant for any substance used for the treatment, or prevention of a disease, syndrome or a symptom, or to a medicament comprising an active component.

As used herein, "an integrated device" is meant for any dosage form having a structure composed of different parts which are united together in one functional and physical whole, to provide, under essentially dry conditions, a structurally stable unified form. A preferred form of an integrated device in accordance with the invention is that wherein the one or more layers are laminated so as to form a laminated device.

As used herein, "laminated" is meant for a device comprising two or more layers/sheets (which may be the same of different), physically of chemically attached/bound together.

As used herein, "a laminated device" is meant for a device consisting of two or more separate layers/films joined together to form a substantially flat plate or sheet, where the separate components still remain in separate phases.

Figure 4:
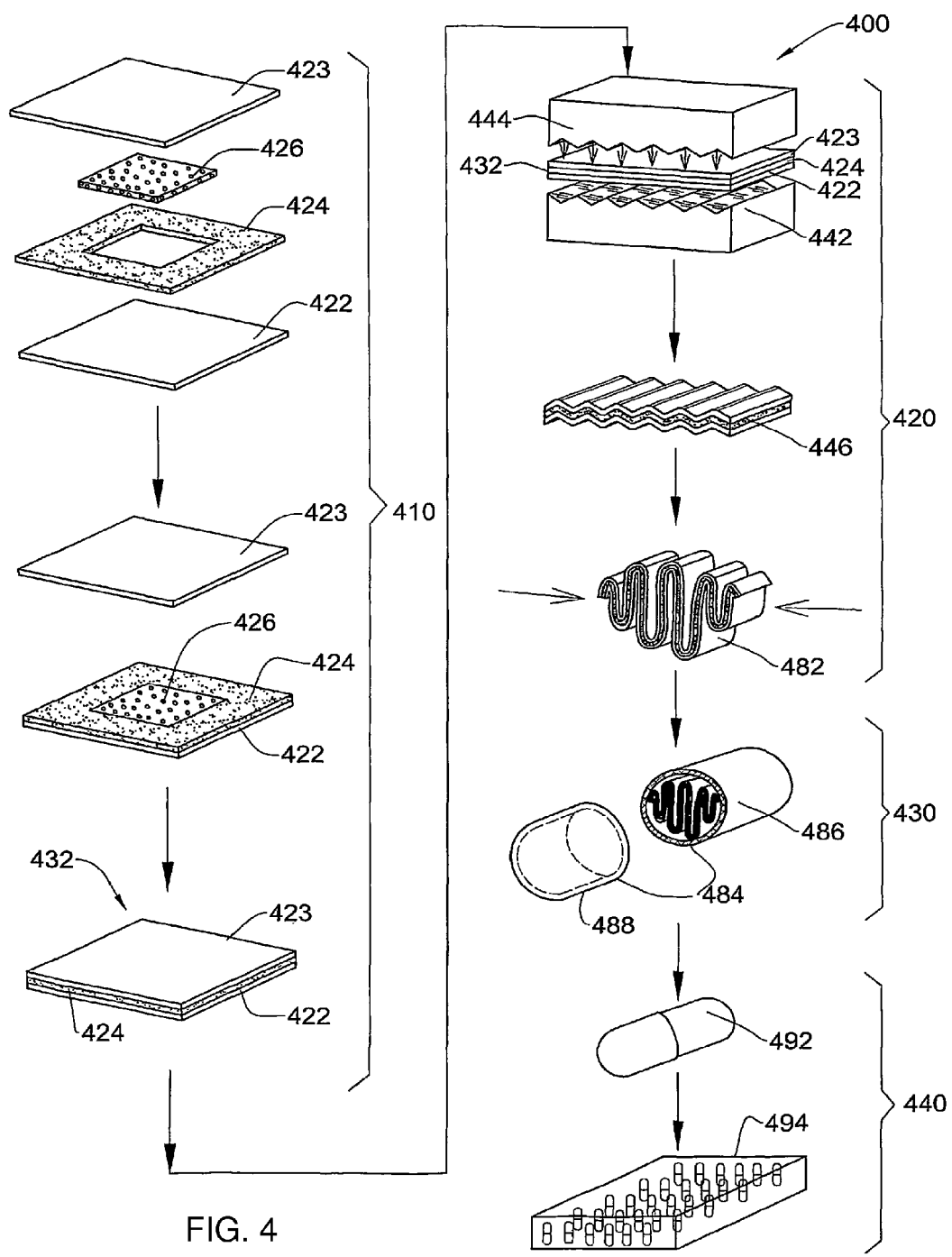
FIG. 4 is a schematic pictorial illustration of the main steps of the method of FIG. 1B.

As used herein, "a folded device" is meant for a device that had been manipulated by one or more of folding about fold lines, bending, twisting, wrapping, winding, rolling, crimping and the like. For example, and without being limited thereto, folding may be parallel to the width of the unfolded device and designed to have folds which are symmetric mirror images about a first axis. This manner of folding may provides an accordion-like configuration for an originally essentially planar device; or the folding may be such that the folded device has folds of increasingly smaller amplitudes upon extending away from the first axis so as to form a partially rounded cross section; yet, a further example is of a folds of increasingly larger amplitudes upon extending away from one end of the first axis to its other end, so as to form a fan-like configuration. An example of a folded device is illustrated in FIG. 4.

As used herein, "a delivery device" is meant for any biocompatible dosage form for the delivery, preferably by oral intake, of an agent or an agent-releasing formulation. More specifically, the delivery device comprises the integrated/laminated device folded and enclosed within an enclosure. In the context of one preferred embodiment of the invention, the delivery device is a gastroretentive dosage form.

As used herein, "unfolded" is meant for an essentially and generally planar configuration of the device. The term "essentially planar" or "generally planar" denotes a fully planar as well as wiggly or wavy shape of the device. Unfolding denotes any form of expansion of the device, which may result form unwinding, unrolling, inflating, swelling, and the like. Following expansion in the stomach, the unfolded and essentially planar device maintains its firmness due to its unique characteristics, as exemplified below As used herein, "gastro-retentive" or "gastro-retentivity" is meant the maintenance or withholding of the agent carried by the delivery device in the GI tract (either after being released from or still in association with one or more of the device's compartments/layers), for a time period longer than the time it would have been retained in the stomach when delivered in a free form or within a gastro-intestinal delivery vehicle which is not considered gastro-retentive. Gastro-retentivity may be characterized by retention in the stomach for a period that is longer than the normal emptying time from the stomach, i.e. longer than about 2 hours, following an average meal, particularly longer than about 3 hours and usually more than about 4, 6, 8 or 10 hours. Gastroretentivity typically means retention in the stomach from about 3, 4, 6, 8 or at times 10 hours up to about 18 hours. It is however noted that in accordance with the invention, retention of the gastroretentive delivery device is not observed after more than 48 hours after administration, and preferably not after 24 hours.

As used herein, "controlled-release" is meant for a dosage form that releases the agent contained in it in a controlled rate, which is usually slowed down or delayed or accelerated as compared to the natural dissolution rate of the agent in the liquid (typically aqueous) medium, e.g. the gastric fluid or simulated gastric fluid.

As used herein "enclosing" is meant for containing, especially so as to envelop or shelter the device in a container. The container (sometimes termed herein "envelop" or "enclosure") may be, without being limited thereto, a capsule (soft or solid) containing the folded device, an elongated tube, a ring or a thread (one or more) surrounding the folded device, a polymeric coating (e.g. a polymeric thread wrapping the device in a manner resembling a cocoon), a polymer or gel matrix embedding the folded device, enclosing by molding or pressing to a form of a tablet and the like.

As used herein, "coating" is meant for the application of a layer of a substance to a surface for protection or modification of the external properties (such as adhesiveness) of the surface.

As used herein, "powdering" is meant for powder coating, e.g. by spreading of powder on a surface. The spreading of the powder may be preceded with the application on the surface to be powdered with suitable adhesive agents.

As used herein, "a polymer" or "polymeric composition" is meant for a single or combination of polymers exemplified by, but not limited to, degradable polymers, non-degradable polymers, as well as a combination of at least degradable polymer and at least one non-degradable. A polymer may degraded in the stomach or in the intestine either through its solubility, chemical degradation such as hydrolysis of esters or solubilization in the gastric or the intestinal media, or through disintegration that is caused by the mechanical forces applied by the stomach on any solid content, or by a combination of both.

It is noted that as used in the specification and claims, the forms "a", "an" and "the" include singular as well as plural references unless the context clearly dictates otherwise. For example, the term "an agent" denotes one or more agents being the same.

Further, as used herein, the term "comprising" is intended to mean that the methods, system or apparatuses of the invention may include the recited elements but not excluding other elements. The term "consisting essentially of" is used to define that the methods, system or apparatuses include the recited elements but exclude other elements that may have an essential significance on the structure and function of the resulting delivery device. For example, a delivery device consisting essentially of three laminated layers will not include or include additional layers. "Consisting of" shall thus mean excluding more than trace elements of other components/layers. Embodiments defined by each of these transition terms are within the scope of this invention.

Further, all numerical values, e.g. when referring the amounts or ranges of the components constituting the composition of the invention, are approximations which are varied (+) or (−) by up to 20%, at times by up to 10% of from the stated values. It is to be understood, even if not always explicitly stated that all numerical designations are preceded by the term "about".

According to one embodiment, the polymer soluble in gastric content comprises one or more polymers selected from a hydrogel-forming polymer, a non-hydrogel polymer, or any combination thereof. Non-limiting examples of hydrogel-forming polymer comprise proteins, polysaccharides, including gums, gelatin, chitosan, polydextrose, cellulose derivatives, such as high molecular weight grades of hydroxypropyl cellulose, hypromelose, hydroxyethyl methyl cellulose, hydroxyethyl cellulose, methyl cellulose, polyethylene oxides, polyvinyl alcohols, soluble derivatives of any one of the above as well as any combination of two or more thereof. Non-limiting examples of non hydrogel polymer comprise povidones (PVP), povidone, and vinyl acetate copolymers (copovidone), methacrylic acid copolymer with dimethyl amino ethyl methacrylate (Eudragit E™), low molecular weight grades of hydroxypropyl cellulose, propylene glycol alginate, polyethylene glycols, poloxamers and soluble derivatives of any one of the above as well as any combination of two or more thereof. These soluble polymers can be further cross-linked, either with use of appropriate chemical cross-linking agent, or by physical cross-linking techniques, or via exposure to gamma radiation, to control their mechanical properties and behavior upon contact with simulated and natural gastric fluid.

According to another embodiment, the polymer may be a water insoluble polymer. A non-limiting list of polymers that are insoluble (non-degradable) comprises any polymer selected from a pharmaceutically acceptable enteric polymer, a pharmaceutically acceptable non-enteric polymer, or any combination thereof. An enteric polymer is preferably such that it is substantially insoluble at a pH of less than 5.5. Non-limiting examples of enteric polymers applicable with respect to the invention include, shellac, cellacefate, hypromelose phthalate, hydroxypropyl methylcellulose acetate succinate, zein, polyvinyl acetate phthalate, aliginic acid and its salts, carboxymethyl cellulose and its salts, methylmethacrylate-methacrylic acid copolymers, is including ethyl acrylate copolymers (polymethacrylates), or substantially insoluble (at pH of less than 5.5) derivatives of any one of the above as well as any appropriate combination of two or more of the above. Non-limiting examples of non-enteric polymers applicable with respect to the invention include ethylcellulose; cellulose acetate; a copolymer of acrylic acid and methacrylic acid esters, having of from about 5% to about 10% functional quaternary ammonium groups; a polyethylene; a polyamide; a polyester; polyvinylchloride; polyvinyl acetate; and a combination of any two or more thereof.

This invention is directed to methods and apparatus for producing oral delivery devices, particularly of gastroretentive delivery forms (GRDFs) and more particularly to encapsulated folded dosage forms.

Generally, the methods and apparatuses of the invention are directed to assembling dosage forms comprising an active agent, e.g. a drug contained within a formulation or within one or more material layers, and one or more layers, which are typically in the form of a single or plurality of strips that have the purpose of imparting mechanical strength as will be explained below, the strips being typically, but not exclusively, arranged so as to define a continuous or non-continuous frame. In some preferred embodiments the device has one or two external, e.g. polymeric layers. For example, the agent-containing layer and the one or more strip are sandwiched between two layers, typically, the two external layers.

Once the layers are assembled, the integrated or laminated delivery device is folded or compacted in some other way and thereafter at least partially enclosed in a container. Preferably the folded dosage form is encapsulated.

Thus, in accordance with its broadest aspects, the invention provides a method producing an agent delivery device for oral intake, the method comprises the steps (preferably, however not exclusively, sequential steps) of assembling one or more layers comprising one or more materials with an agent or an agent-releasing formulation to form an intergraded device; folding said integrated delivery device to form a folded integrated delivery device; and at least partially enclosing said folded delivery device to a form suitable for oral delivery.

In accordance with a preferred embodiment, the one or more layers comprise one or more polymeric materials. Further, the one or more layers may comprise a single polymer or a combination comprising two or more polymers, the polymer or polymers in each layer may be the same or different from that forming another layer in the device. The polymeric material may be a soluble polymer or soluble polymer combination (ph dependent or pH independent) or a non-soluble polymer or a polymer combination, as defined hereinabove. The selection of polymer combinations for constituting each of the layers in the integrated device will be further explained hereinbelow.

In accordance with an embodiment of the present invention, the delivery device is formed from a folded integrated device that comprises two external layers sandwiching a functional layer comprising the agent or agent-releasing formulation. In accordance with this embodiment, the method comprises:
  (a) assembling two external layers made of a first material so as to sandwich a functional layer comprising one or more strips made of a second material, the functional layer comprising one or more agents in or on one or more compartments and/or layers, respectively, of the functional layer;
  (b) folding the integrated device into a folded integrated device; and
  (c) at least partially enclosing the folded integrated device.

In some preferred embodiments, the functional layer comprises a matrix further comprising one or more layers and the agent or agent-releasing formulation, said agent being releasable from the matrix. In some embodiments the matrix comprises a polymer or polymer combination that is insoluble in gastric content. In some other embodiments, the functional layer may comprise a combination of compartments enclosing an agent formulation and a matrix embedding the active agent. The agent within the compartments and the agent embedded in the matrix may be the same or different.

In some other embodiments, the matrix comprises at least one soluble polymer or a soluble combination of polymers in combination with at least one insoluble n) polymer (or insoluble combination of polymers).

It is preferable that the agent or agent-releasing formulation is releasable from the functional layer.

The one or more layers may also comprise a layer of an enforcing polymeric composition so as to provide the desired configuration of the single or multi-layered device, once unfolded (e.g. following wetting by gastric content or by a medium resembling gastric content). The desired configuration may be achieved by the incorporation of an enforcing polymeric composition having a mechanical strength enabling, upon wetting and unfolding of the device, the preservation of the unfolded configuration of the device, i.e. after ingestion. The enforcing polymeric composition may be provided over the agent carrying layer (e.g. polymeric matrix), over the compartments comprising the agent, and/or may be integrally formed with or in the agent-carrying layer.

According to one embodiment, the enforcing polymeric composition is in the form of one or more continuous or non-continuous polymer strips. For example; the strips may define a continuous or non-continuous frame at said device's periphery. The continuous or non-continuous frame may be either affixed or attached to the matrix or integrally formed with the matrix. Further, when as a strip or in a continuous form to form the so-called frame, the enforcing strip/frame may comprise a single or plurality of defects, e.g. gaps, depressions or slits, typically along the width of the strip/frame. Without being bound by theory, it is believed that such slits are essential for providing breakable areas along the strip/frame such that after a pre-determined time (e.g. when expulsion of the device from the body is desired, for example, after 12 hours) the areas containing the slits weaken and break, resulting in the disintegration of the device and its eventual removal from the stomach through the pylorus sphincter.

The combination of the enforcing composition, polymeric matrix and the agent or agent-releasing formulation constitute, at times, the functional layer (the functionality denoting that these combined layers constitute a significant functional portion of the delivery device, on the one hand, the gastroretentivity, established by the enforcing layer, and the active principle ingredient, i.e. the drug, diagnostic agent etc., on the other hand). According to this embodiment, the assembly step may comprise assembling at least one layer of the enforcing composition, e.g. in a form of one or more continuous or to non-continuous strips, with one or more layers comprising said agent or agent-releasing formulation or with the agent or agent-releasing formulation enclosed within the enforcing strips.

In accordance with one embodiment, the strips are in the form of a frame have inner boundaries defining a void, and the method comprises assembling the frame with one or more layers comprising said agent or agent-releasing formulation, such that the one or more layers comprising the agent or agent-releasing formulation is affixed, attached or integrally formed within said void. Alternatively or in addition, the agent or agent-releasing formulation may be enclosed, at least partially, within the frame.

The agent or agent releasing formulation may be contained in the device in various forms. The incorporation of the agent or formulation thereof in the device is carried out in the assembly step. Thus, in accordance with an embodiment of the invention, the assembly stem comprises at least one of the following:

embedding said agent or agent releasing formulation into one or more layers or into one or more compartments within one or more layers (e.g. a single layer may comprise areas of different composition of the polymer material forming it thereby forming distinguishable areas/compartments within the layer and these compartments may differently carry/release the agent so as to provide a differential release profile of the agent from the device);

trapping said agent or agent releasing formulation within at least two layers (e.g. such that the layers form a pouch housing the agent);

enveloping said agent or agent-releasing formulation within at least one polymeric membrane segment;

attaching said agent or agent-releasing formulation to or in at least one of said one or more layers of the device, or to a carrier, the carrier may be in the form of nano- or microspheres, nano- or microcapsules comprising particulate matter (i.e. a matrix) accommodating the agent (by embedding, entrapping or having the agent affixed to the particulate's outer surface), beads coated or impregnated with the agent, granules, pellets and compressed tablets.

In order to provide the desired mechanical strength in situ, once the device is in an unfolded state in the stomach, it is preferable that the enforcing polymeric composition, or at least one other layer of the device comprises a polymer that is insoluble in gastric juices/content. Alternatively, the mechanical strength can be provided by a combination of enteric and non-enteric insoluble polymers.

In addition to the aforementioned composition, the enforcing composition, irrespective of its shape or its number (e.g. number of strips made of the enforcing composition) within the device may further comprise a polymer, soluble in gastric content, which is either entrapped in the insoluble composition or is cross-linked in such way that it does not exude from the insoluble composition and can not be extracted without disintegrating the whole frame.

In accordance with a preferred embodiment, the device is a laminated device comprising two external layers made of a first material and sandwiching one or more layers comprising one or more strips made of a second material and comprising the agent or agent releasing formulation. The external sheets may comprise one or more polymers selected from the group consisting, without being limited thereto, polymers soluble in gastric content, polymers insoluble in gastric content, and a combination of any two or more thereof.

Nonetheless, in accordance with some other embodiments, the laminated device comprises two external layers made of a first material and sandwiching one or more layers comprising one or more strips made of a second material, such that the one or both external layers comprise the agent or agent releasing formulation. In the context of this embodiment, the agent may be embedded in as well as deposited to the outer surface of one or both external layers, e.g. by inkjet printing. An ink jet technology that has been developed is such that allows the preparation of poly(lactic-co-polycolic acid) (PLGA) microspheres with uniform particle size distribution [Radulescu D et al. Uniform paclitaxel-loaded biodegradable microspheres manufactured by ink jet technology *Proceedings of the Winter Symposium and 11$^{th}$ International Symposium on Recent Advances in Drug Delivery Systems* Salt Lake city, Utah, USA (2003)]. These microspheres while carrying the agent may then be affixed or attached to the one or both external layers.

In accordance with one embodiment, the external layers comprise a polymer or polymer composition that is soluble in gastric content.

According to another embodiment, the external layer is comprised of a mixture of a soluble polymer and an enteric polymer. According to another embodiment, the external layer comprises a cross-linked water soluble polymer, e.g. a soluble polymer cross-linked with glutaraldehyde, or an enzymatically hydrolyzed cross-linked gelatin and a derivative thereof.

Another example of external layer composition can be polyvinyl alcohol film, cross-linked with glutaraldehyde. Alternatively, said polyvinyl alcohol film could be subjected to one or more freeze-thaw cycles to induce crystallization.

Yet another example of external layer composition can be polyethylene oxide film, cross-linked by gamma irradiation.

In addition to the mentioned composition, the layers independently may comprise fillers, lubricants, plasticizers and other pharmaceutically acceptable processing adjuvants.

Irrespective of their composition, the one or more external layers may comprise perforations. The perforations may be generated a priori, i.e. before the layers are integrated into the device; as a sub-step in the assembly step or following the assembly step (i.e. after all layers are assembled together into a whole unit), however, before the folding step; or the external layers may constitute a combination of materials such that when the device is wetted (or at least the external layers), perforations are produced. The dimensions, distribution pattern, shape and amount of perforations may vary between one device to another, within a layer of a single device as well as between the two external layers of a device, depending on the specific design of the delivery device and the manner of their formation (e.g. mechanical slicing of holes or perforations resulting from dissolution of a component of the external layer following wetting by gastric content).

The assembly of the device's layers may be facilitated by various integration/lamination techniques known to those versed in the art. The assembly may be achieved by applying onto at least portions of some of the layers an integration agent, prior to bringing the respective layers into contact. The coating may be on one or more layers. A particular example includes application to at least one surface of the external layers, the strip/frame and the layer carrying the agent or agent-releasing formulation.

In accordance with one embodiment, the integration agent is an adhering agent which may be sprayed onto at least some of the layers of the device. In accordance with this embodiment, the adhering agent is preferably an organic solvent, a mixture of organic solvents, or a mixture of organic and water-based solvents such as salt solutions. More preferably the organic solvent is ethanol or mixture of ethyl acetate and ethanol.

In accordance with some other embodiments, the assembly is facilitated by other techniques such as welding (heat-welding, welding by high frequency, welding by ultrasound etc.), by curing (e.g. heat curing), fusion or any other technique involving melting both layers to form adherence at the interface between the layers as well as pressing the layers together (with or without heating to temperatures above room/ambient temperature). The said other techniques may involve the a priori application of an agent or substance to the layer so as to facilitate the assembly, as appreciated by those versed in the art.

In another preferred embodiment, the composition of the outer layer is treated so as to modify the properties of the outer surface, e.g. so as to prevent adhering of the undulated surface of the device as a result of folding. To this end, the assembly step may further comprise coating of the outer surface of one or both external layers with an anti-adhering coating, e.g. powder coating, polymer coating, liquid spray coating, dispersion (latex) coating, etc. The application of the powder may involve the a priori application of an adhering agent as defined above so as to facilitate adherence of the powder coating onto the respective layer.

In accordance with one preferred embodiment of the present invention, there is provided a method for producing a laminated device, preferably a gastro-retentive dosage form, comprising:
  (i) assembling a laminated device that comprises:
    a) a first external layer made of a first, typically polymeric material;
    b) a frame of a second, typically polymeric, material mounted on the first external layer;
    c) a drug-releasing formulation housed within the frame; and
    d) a second external layer made of the first material and mounted on the frame; and
  (ii) folding the laminated device into a folded device; and
  (iii) at least partially enclosing the folded device to produce the delivery device, preferably gastro-retentive dosage form, that can be administered orally.

In some preferred embodiments, the frame comprises one layer. In other embodiments, the frame comprises two or more layers. In accordance with one, non-limiting, embodiment, the frame has a thickness of around 400 microns, independent of the number of layers therein.

Further, in accordance with some other embodiments, the invention is directed to a method for producing an oral agent-releasing dosage form, comprising:
  (i) preparing or providing two first, essentially planar, polymeric sheet portions made of a first polymeric material that when wetted is permeable to the active agent, and a having outer boundaries;
  (ii) preparing or providing a second, essentially planar, polymeric sheet portion made of a second polymeric material defining a frame with outer boundaries and inner boundaries, the outer boundaries being of essentially the same shape as the outer boundaries of the first polymeric sheet portion and the inner boundaries defining a void area;
  (iii) preparing or providing a third, essentially planar, polymeric sheet portion made of a third polymeric sheet comprising an agent or agent releasing formulation releasable from the third sheet when in contact with an aqueous medium and defining a drug-containing and releasing matrix, said matrix having outer boundaries to fit within the void area;
  (iv) assembling the four portions such that said third sheet is placed within the void area and the two (the second sheet portion and the third sheet portion) being jointly sandwiched between the two first polymeric sheet portions, with all the outer boundaries essentially overlapping one another thus yielding a laminated device;
  (v) folding the laminated device into a form to fit into a capsule, and inserting it within a capsule made of a material that dissolves in the gastric fluids.

In some cases, this method comprises preparing first, second and third polymeric sheets made of the first, second and third polymeric materials, respectively, and cutting out the respective first, second and third polymeric sheet portions therefrom such that all sheets have essentially the same outer shape so as to facilitate the overlap between the outer boundaries thereof.

Yet further, in accordance with another embodiment, a method for producing an agent delivery device, comprising:
  (i) assembling an agent or an agent-releasing formulation within a generally planar assembly to form an integrated or laminated device, wherein the generally planar assembly may comprise a single or plurality of layers and may comprise or consist of a frame;
  (ii) manipulating the integrated or laminated device into a compacted integrated device, wherein the projected surface area of the compacted laminated dosage form is at least five times less than that of the integrated device; and
  (iii) at least partially enclosing the compacted device to produce the gastro-retentive dosage form.

In accordance with this embodiment, the projected surface area of the compacted device may also be at least six times, at least seven times, at least eight times, at least nine times and even at least ten times less than that of the integrated/laminated device form. The agent/agent releasing formulation may be assembled as part of a layer carrying the same and surrounded, at least partially, by the frame. Further, the generally planar assembly may comprise one or more external layers. A preferred embodiment in accordance with this method concerns a generally planar assembly comprising at least three integrated/laminated layers.

Further, in accordance with another embodiment of the present invention, the assembling step comprises introducing the agent or agent-releasing formulation into a layer of a second material (different from the material forming the external layers and/or the strips/frame).

As indicted above, the agent, which may be a pharmaceutical drug (or pro-drug) having a therapeutic or prophylactic effect or may be an agent useful for imaging or another diagnostic utility as well as a nutritional substance, is, in some cases, preferably provided between the at least two layers of the matrix wherein the drug is in a form selected from, but not limited to, the group consisting of a polymeric film, powder, solution, dispersion, or embedded in a semisolid, micro- or nano-spheres, micro- or nano-particles and a combination of any two or more thereof.

In some preferred embodiments, the agent is a drug that has a narrow absorption window in the gastrointestinal tract.

As appreciated by those versed in the art, the agent may be any low molecular weight compound, as well as an oligomer or polymer. In some preferred embodiments, the agent is selected from therapeutic nucleic acid, a therapeutic nucleic acid sequence, therapeutic amino acid, a therapeutic amino acid sequence, the nucleic acids and amino acids may be naturally occurring acids, chemically modified acids as well as semi-synthetic or synthetic acids, as known to those versed in the art. The agent may also be a peptidomimetic drug, an antibiotic agent; therapeutic ions (e.g. lithium, potassium), a vitamin, a bronchodilator, an anti-hypertensive agent, a diuretic agent, an anti-gout agent, an anti-hyperlipidemic agent, an angiotensin converting enzyme (ACE) inhibitor, angiotensin receptor blocker (ARB), an anti-parkinson agent, dopaminergic agent, a peripheral decarboxylase inhibitor, a COMT inhibitor and a combination of any two or more thereof.

In some embodiments, the drug is for local treatment of the gastrointestinal tract as is exemplified by, but not limited to, anti-tumor agent, a histamine blocker, a bismuth salt, a lipase inhibitor, a synthetic prostaglandin, an anthelminitic agent, and anti-infective (such as antibiotic) agent, and a combination of any two or more thereof.

Examples of the agent or drug families are exemplified by, but not limited to L-DOPA, gabapentin, ropinirole hydrochloride, pramipexole dihydrochloride, bupropion, sumatriptan, phenylepherine, stavudine, didanosine (DDI), zidovudine (AZT), zalcitabine, ganciclovir, acyclovir, valganciclovir, zidovudine & lamivudine, lamivudine (3TC), abacavir, abacavir & zidovudine & lamivudine, valcyclovir, atazanovir, captopril, ramipril, fosinopril, Enalapril, quinapril, Losartan, Losartan/HCT, valsartan, valsartan/HCT, ciprofloxacin hydrochloride, rifaximin, cefdinir, cefaclor, cefditoren pivoxil, cefuroxime axetil, cefprozil, ceftibuten, loracarbef, gatifloxacin, moxifloxacin, levofloxacin, telithromycin, linezolid, doxycycline hyclate, moxifloxacin, levofloxacin, telithromycin, linezolid, rifaximin, voglibose, xenical, gastric lipase, pancreatic lipase and amylase, b12 intrinsic factor, voglibose, tacrine, omeprazole, rabeprazole sodium, rivastigmine, zolpidem, famotidine, rantidine, fexofenadine, metformin. baclofen. bisphosphonate. tacrolimus. rapamycin. cyclosporine. cetirizine dihydrochloride. piperacillin, miglustat, misoprostol, diclofenac & misoprostol and bosentan, mebendazole, alendronate, pamidoronate, zolendronic acid.

In some embodiments the drug is degraded in the colon.

Additionally, in accordance with another embodiment of the present invention, the folding step comprises: mounting the laminated device between two opposite faces of a press, each of which constituting a block having corrugated surface with ridges of one being essentially opposite to troughs of the other and essentially fitting one into the other; and pressing the two opposite faces one versus the other so as to form an undulated; three-dimensional device, wherein the undulations thereof correspond to the shape of the corrugated surface.

In another preferred embodiment, the folding step further comprises applying a force so as to press the undulated device from two sides and in a direction perpendicular to the undulations, into a folded device having folds formed along ridges and troughs of the undulations.

In some preferred embodiments, the folded device is folded parallel to one of the sides of the unfolded laminated/ integrated device. In another preferred embodiment, the folded device has folds of increasingly smaller amplitudes upon extending away from the middle thereof so as to have an overall rounded cross section and to allow the folded device to be easily insertable into a container (envelop, e.g. capsule).

Thus, in accordance with the latter preferred embodiment, the two opposing surfaces of the press have such corrugations that following pressing, undulations with amplitudes that decrease from the middle towards the ends are formed, and upon the subsequent pressing in the said perpendicular direction an essentially circular cross-section is eventually attained, thus having an overall cylindrical form with a longitudinal axis parallel to the folds.

In one preferred embodiment, the eventual cross-section is such to allow the insertion of the folded device into a capsule of a kind conventionally used in pharmaceutical dosage forms. In accordance with this latter embodiment the process preferably further comprises at least partially enclosing the folded device within a capsule by pushing it along the longitudinal axis into one half of a capsule.

In accordance with a preferred embodiment of the present invention, the at least partially enclosing step of the above embodiment comprises:

placing the folded device into a capsule base (i.e. one half of the capsule before enclosure); and fitting a capsule cap (i.e. the other half of the capsule) onto the capsule base so as to form an encapsulated folded integrated delivery device/dosage form.

In some other embodiments, the folded device is at least partially enclosed within an enclosure through at least one process selected from: wrapping (e.g. with a polymeric thread), dipping (e.g. to form mold), spraying (e.g. with a polymeric coating material), encapsulating, binding (e.g. with a polymeric thread), tying (e.g. with a polymeric thread), molding (e.g. to form mold), enveloping and sealing, e.g.

The invention also provides an agent delivery device prepared in accordance with any one or more of the alternative methods described above. In accordance with one preferred embodiment, the invention provides a dosage form comprising a folded laminated device enclosed in a capsule, for the controlled, gastroretentive release of an agent, the dosage form being prepared in accordance with any one or more of the alternative methods described above.

The present invention also provides a system for producing an agent delivery device, the system comprising:

(i) an assembly apparatus adapted to assemble one or more layers comprising one or more materials and an agent or an agent-releasing formulation to form an intergraded device;

(ii) a folding apparatus adapted to fold the integrated device into a folded integrated device;

(iii) an enclosing apparatus adapted to at least partially enclose the folded integrated device within an envelop to form a device in a form suitable for oral delivery.

In accordance with this aspect of the invention, the assembling apparatus is preferably adapted to assemble an integrated device, preferably, a laminated device, the integrated device comprising:

(i) a first external layer comprising a first material;

(ii) one or more functional layers mounted on said first external layer and comprising a second material and said agent or agent releasing formulation;

(iii) a second external layer comprising said first material and mounted on said functional layer.

Alternatively, the assembly apparatus may be adapted to assemble an integrated, preferably laminated, device, the integrated device comprising:

(i) a first external layer of a first material;

(ii) a frame mounted on the first shielding layer;

(iii) a drug releasing formulation housed within the frame; and (iv) a second layer of the first material layer mounted on the frame;

In some preferred embodiments, the assembling apparatus further comprises a dicing system, adapted to cut at least one shaped piece from a sheet of the first material and at least one shaped piece from a sheet of the second material.

In accordance with one embodiment, the dicing system is adapted to cut at least two shaped pieces from a sheet of a first material and at least one shaped piece from a sheet of a second material. The shape of the two pieces from the first material and the shape of the piece from the second material may be the same or different.

According to one embodiment, the at least three pieces (two of the first material and one of the second material) are similarly cut such that their outer boundaries overlap in the assembled device.

In accordance with another embodiment, the pieces may be differently cut. In some cases the two pieces of the first material preferably have serrated perimeters, at least throughout a portion of the perimeter of the piece, in the shape of a plurality of teeth (or other form of protrusions, such as notches or grooves) such that upon assembly, a tooth at the perimeter of one piece overlap with a groove at the perimeter of the other piece of first material. In one other embodiment, the integrated device comprises at least three layers, two serrated external layers made of a first material and sandwiching an agent-comprising layer, whereby from an exploded side view of the integrated device the teeth/notches at the perimeter of the two external layers at least partially intersect (i.e. overlap). In accordance with some other embodiments, teeth/notches at the perimeter of the two external layers do not intersect (i.e. from an exploded side view of the device the protrusions formed by the teeth of the two layers alternate).

In some embodiments, assembly apparatus is also adapted to assemble the agent or agent releasing formulation when the agent or agent releasing formulation is either:
  embedded into one or more layers;
  trapped within at least two layers;
  enveloped within at least one polymeric membrane segment; or
  attached to or in any one of at least one layer of the device, nano- or microparticles, powder, liquid or compressed solids or to or in a matrix;
  and any combination of the above.

In some case, the assembling apparatus further comprises an application apparatus adapted to apply an integration agent onto at least one layer prior to the assembly. The application apparatus may comprise a spraying mechanism for spraying said integration agent onto at least one of the devices layers. The integration agent may be any agent suitable for facilitating adherence, welding, fusion, curing etc., between two or more of the devices layers.

In accordance with one embodiment, the integration is facilitated by spraying an adhering agent (e.g. an organic solvent such as ethanol or mixture of ethyl acetate and ethanol, or a mixture of organic and water-based solvents such as salt solutions).

In accordance with an alternative embodiment, the integration is facilitated by welding (e.g. heat-welding, welding by high frequency, welding by ultrasound etc.).

The system may further comprise a perforation apparatus adapted to provide at least one of said external layers with perforation. This may be achieved by the use of an array of pins or slicing knives presses against the layer to be perforated. As indicated above, the perforations may be of various dimensions and distribution patterns, and may be different between the two external layers. To this end, the perforation apparatus may comprise a series of differently arranged array of pins, the pins (or knives) being of the same or different dimensions etc.

The assembling apparatus may also comprise an assembly jig (holding board), adapted to assemble two external layers, a frame, an agent or agent-releasing formulation into a predetermined form; and a pressing assembly adapted to press the predetermined form into the integrated dosage form.

The system preferably further comprises a coating apparatus for forming a coating or powder layer on at least one side of the integrated device. The coating apparatus may be a powdering apparatus for forming a powder layer on at least one side of the integrated dosage form.

In accordance with an embodiment of the invention, the folding apparatus comprises a press with two opposite faces, each of which having a corrugated surface with ridges of one being essentially opposite to troughs of the other and essentially fitting one into the other; whereby upon placing the laminated device in the press and pressing the two opposite faces one versus the other, an undulated, three-dimensional device is formed with undulations that correspond to the shape of the corrugated surface. The two faces are at times referred to as an upper bend tool and bending base. In accordance with some other embodiments the folding apparatus comprises:
  (i) a mounting jig/bending base having a corrugated surface for mounting the integrated dosage form thereupon; and
  (ii) a pressing block/upper bending tool having corresponding ridges to said corrugated surface for pressing on the integrated dosage form so as to form an undulating three-dimensional integrated dosage form, wherein the undulations thereof correspond to the shape of the corrugated surface.

In another preferred embodiment, the folding step further applying a force so as to press the undulated device from two sides and in a direction perpendicular to the undulations; into a folded device having folds formed along ridges and troughs of the undulations.

In a preferred embodiment, the system of the invention comprises:
  (i) an assembling apparatus for assembling an agent within a generally planar laminated assembly to form a laminated device;
  (ii) a manipulating apparatus adapted to manipulate the laminated device into a compacted laminated device, wherein the projected surface area of the compacted laminated device is at least five times less than that of the laminated device; and
  (iii) an enclosing apparatus for at least partially enclosing the compacted laminated device to produce the agent delivery device.

The system of the invention also comprises an enclosing apparatus. In accordance with a preferred embodiment of the invention, the enclosing apparatus comprises an encapsulating apparatus. In accordance with one embodiment, the encapsulating apparatus comprises a capsule jig for holding a capsule base and the same or different capsule jig for holding a capsule cap, whereby upon insertion of the folded integrated device into said capsule base, said capsule cap is fitted onto said capsule base comprising the folded integrated device. The capsule jig may also comprise a revolver for revolving the capsule jig during operation.

The present invention also provides a folding apparatus for folding a single or multi-layered sheet, the folding apparatus comprises a press with two opposite faces, each face having a corrugated surface with ridges of one corrugated surface being essentially opposite to troughs of the other corrugated surface and essentially fitting one into the other; whereby upon placing at least a portion of the single or multi-layered sheet in the press and pressing the two opposite faces one versus the other a three dimensional device having at least said portion undulated is formed with undulations that correspond in shape to that of said corrugated surfaces.

The folding apparatus in accordance with this aspect of the invention is preferably designed such that the corrugated surface is formed by a series of fingers (e.g. in the form of parallel blocks) extending downwardly and comprising a movable central finger having a first length, and at least one pair of secondary movable fingers siding said central finger and having a second length being shorter than the first length, the folding apparatus further comprising a control utility for controlling upwardly and downwardly sequential movement of said central finger and at least one pair of secondary fingers towards the said other corrugated surface. The fingers may have a width corresponding to one dimension of the sheet to be folded (preferably the same or wider).

In accordance with another embodiment, the folding apparatus comprises a movable central finger having a first length, at least one pair of secondary movable fingers siding said central finger and having a second length being shorter than the first length, and a third pair of movable fingers having a third length being shorter than the second length, each finger in the third pair siding one of the secondary pair of fingers.

The folding apparatus in accordance with this embodiment may also be equipped with a secondary press having opposite faces perpendicular to the faces of said primary press and adapted to press the undulated device so as to form a folded device having a dimension which is at least five times smaller than that of the sheet prior to pressing.

In accordance with this aspect of the invention, there is also provided a method for folding a single or multi-layered sheet comprising:
 (i) placing said sheet in a folding apparatus; and
 (ii) pressing the two opposite faces of the first press one versus the other to form an undulated, three dimensional device with undulations that correspond in shape to that of said corrugated surfaces.

The method may also comprise activating the secondary press so as to press the undulated device in a direction perpendicular to the direction of pressing by said first press so as to obtain a folded device having a dimension which is at least five and even at least as up to ten times smaller than that of the sheet prior to pressing.

The scope of this invention should not be construed as being limited to the aforementioned embodiments. It should be understood that any combination or permutation of these exemplary embodiments is within the scope of this invention.

Turning now to FIG. 1A, a simplified flowchart 100 is presented, illustrating the major process steps of a method for producing a compacted gastro-retentive dosage form 131 in accordance with a preferred embodiment of the present invention.

In an assembling step 105, at least one section of a first material 103, a second material 106 and another section, preferably of the first material 107 are each diced into at least one predetermined shape and are oriented such that material 107 is used to form a base.

Typically, the active agent 101 is first at least partially physically retained within or on the at least one section of material 103. In other embodiments, the agent is dispensed into the material 103. The at least partial retention of the agent may be achieved by any means known in the art, including embedding, adsorbing, enclosing etc, as well as others, such as those disclosed in U.S. Pat. No. 6,685,962, whose disclosure is incorporated herein by reference.

In accordance with one embodiment, the agent 101 is assembled optionally together with at least one material 103 inside a frame of second material 106 to form a laminated device 111, which, structurally, is generally planar. Optionally, another layer of the first material 107 may be mounted on top of the frame. The apparatus used to perform this step may be identical, similar or different to the apparatus of FIG. 5 described hereinbelow.

Thereafter, in a manipulating step 115, the laminated device 111 is manipulated into a compacted device 121. The manipulating step may comprise one or more of folding, bending, twisting, wrapping, winding, rolling, crimping or any other mechanism known in the art to reduce the projected surface to volume ratio of the generally planar assembly of form 111 by at least a factor of two, more preferably by at least one order of magnitude and yet more preferably by at least two orders of magnitude. The apparatus used to perform this step may be identical, similar or different to the system of FIGS. 7A, 8 and 9 hereinbelow.

Laminated device 111 typically has a projected surface to volume ratio of 1.25 mm$^{-1}$ whereas after the manipulating step 115.

The compacted laminated device 121 is at least partially enclosed in an enclosure 123 in enclosing step 125 to form a folded agent delivery device for oral intake 131. The enclosure may be of the form of a unit enclosure or may be a liquid polymer or gel as well as other enclosures as described hereinabove. The enclosure itself may be a continuous layer or may be discontinuous. In a preferred embodiment, the enclosure is a capsule comprising two parts, a capsule base and a capsule cap. In step 125, the compacted form 121 is placed in the capsule base and thereafter the capsule cap is fitted over the base to fully enclose the compacted form.

Notwithstanding the above, enclosing step 125 may comprise one or more of the following processes: wrapping, dipping, spraying, encapsulating, binding, tying, molding, enveloping, inserting and sealing or any other process known in the art, so as to obtained a compacted device. It has been found by the inventors that following oral intake and upon release from the enclosure and unfolding, the unfolded device is gastro-retentive. The resultant unfolded device may typically be retained in the stomach for 3-12 hours. During this time, the agent is released from the device, preferably in a controlled manner.

Figure 1B:
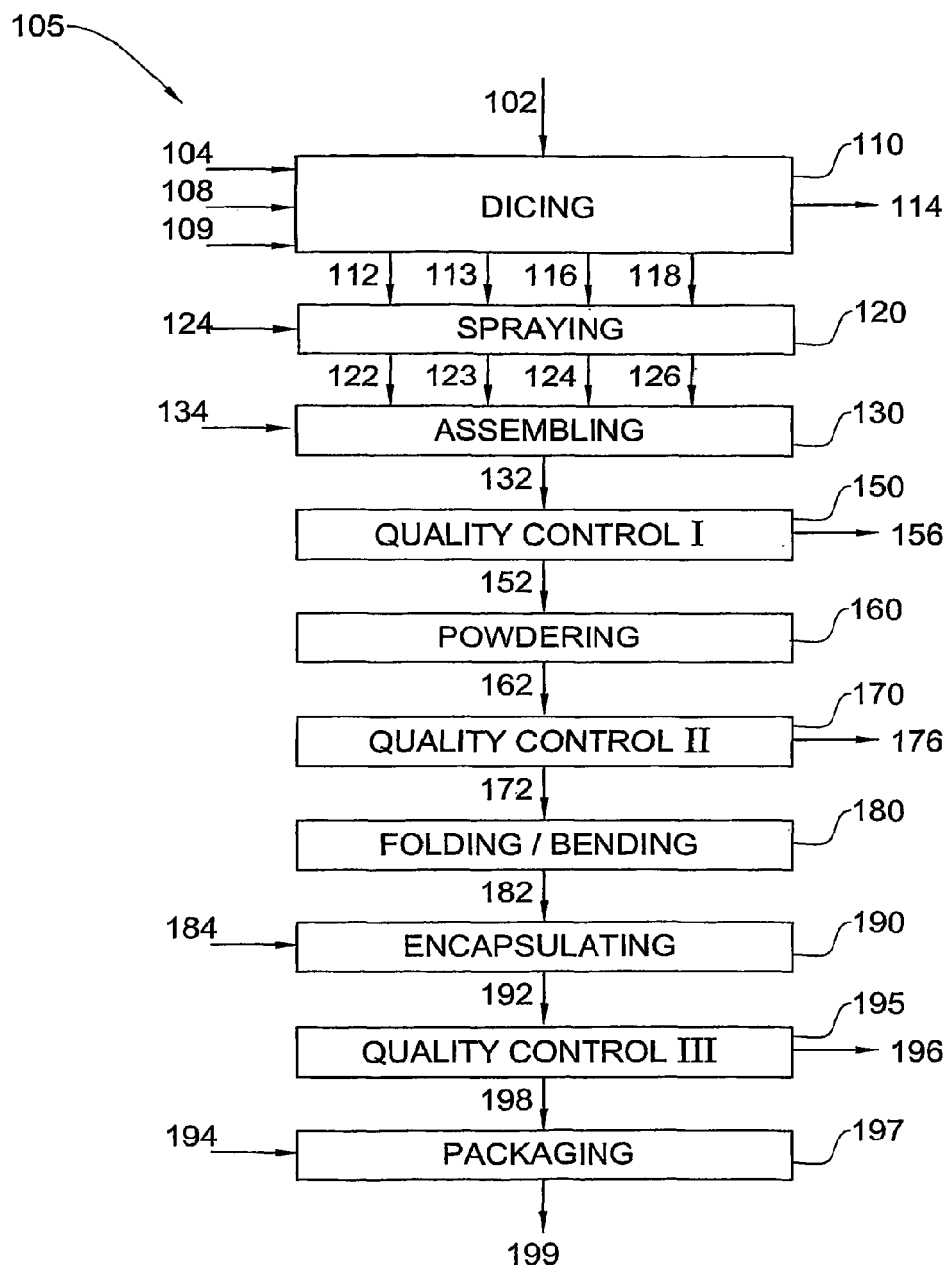
FIG. 1B is a simplified flowchart illustrating a method for producing an encapsulated folded dosage form in accordance with a preferred embodiment of the present invention.

Reference is now made to FIG. 1B, which is a simplified flowchart 105 illustrating a method for producing an encapsulated folded agent delivery device 198 in accordance with a preferred embodiment of the present invention.

In a dicing step 110, a first material sheet 104, such as a polymeric material, is diced into at least two essentially planar sheet portions 112, 113. A second material sheet 108, which may also be a polymeric material (the same or different as the first material) is diced into one or more essentially planar sheet portions 116. A third material sheet 109, which may also be a polymeric material, comprising an active agent 102 is diced into at least one essentially planar sheet portion 118 of a predetermined shape.

In some alternative embodiments, sheets 109 are pre-diced and the active agent 102 is inserted therein, prior to dicing step 110. Sheets 109 are not diced in step 110 in cases where the cost of the active agent is very high and the agent cannot be wasted in this step.

The apparatus used to perform this step may be identical, similar or different to the apparatus of FIG. 5 described hereinbelow.

Figure 2:
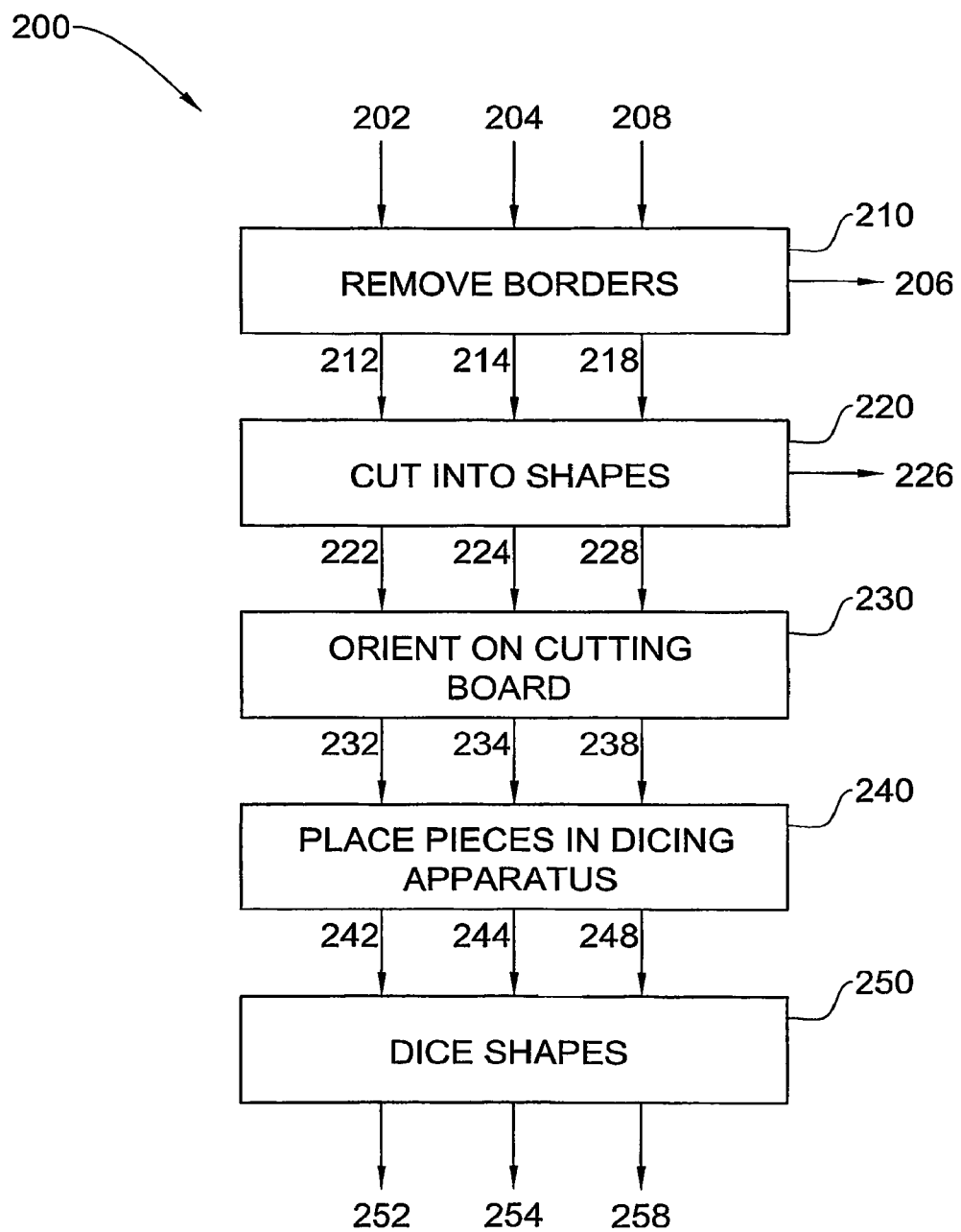
FIG. 2 is a simplified flowchart illustrating details of a dicing step of FIG. 1B.

In a preferred embodiment of the present invention, the dicing step comprises several sub-steps as shown in further detail in FIG. 2.

In a spraying step 120, portions 112, 113, 116 and 118 are sprayed with a spray 124. The spray is typically liquid and preferably an organic liquid. Most preferably, the spray comprises ethanol. Alternatively, the spray comprises a solid adhesive powder or a liquid adhesive. The spraying process is adapted to enhance the adhesive properties of the surfaces of portions 112, 113, 116 and 118. Preferably spraying step 120 renders the sheet portions sticky.

In some embodiments, sheet 118 is not sprayed, but rather placed within sheets 112, 113 and 116.

In some other embodiments, the spraying step is an integral part of assembling step 130. Diced sheet portions 112, 113, 116 and 118 may be sprayed in a specific sequence, coordinated with the assembling step. For example, portion 112 may first be sprayed and then one or more portion 116. Portion 116 may then be assembled on sheet portion 112. Thereafter, sheet portion 118 may be sprayed and mounted within 116 on 112. Thereafter portion 113 may be sprayed and mounted on portions 116 and 118 to form an upper layer. Many different variations of these steps (110, 120 and 130) are envisaged within the scope of the invention.

Sticky first sheet portions 122, 123 (at times referred to herein by the terms "external layers"), sticky one or more essentially planar second sheet portions 124 (at times referred to herein by the term "frame") and sticky third sheet portion 126 (at times referred to herein by the term "matrix") are then assembled together in an assembling step 130. Typically, sticky one or more essentially planar second sheet portions 124 are first assembled to form a frame on one sticky first sheet portion 122. Thereafter, sticky third sheet portion 126 comprising the active agent is placed within the second sheet portions 124. Thereafter the second portion of sticky first sheet 123 is placed on the second sheet portions 124 to form a multi-layer assembly 132. In some embodiments, assembly may be facilitated by applying onto some of the layers following their orientation and placement in the assembled unit some pressure, such as a pressure of 0.8 to 1.5 gr/mm$^2$ to form the assembled laminated device 132.

In some embodiments of the invention, an active agent 134 is placed within the frame at step 130, at times, instead of being introduced into layer 109 prior to the dicing step.

Thereafter, in an optional (albeit preferable) first quality control step 150, the laminated device 132 is visually inspected to check the quality of the adhesion between the parts. Furthermore the dimensions of the resultant laminated device 132 are measured and checked to see that they meet with a required specification. If there is any significant nonconformity, the laminated device 132 is rejected in reject stream 156. If the device meets all the requirements the accepted device 152 is passed to a powdering step 160.

In powdering step 160, the laminated device 152, is coated with a suitable coating, e.g. an anti-adhering powder, to form a powdered laminated device 162. The powder is selected from a pharmaceutically acceptable cellulose or derivative thereof, silicate or talc.

In accordance with one preferred embodiment the powder is microcrystalline cellulose (Avicel, obtained from FMC BioPolymers).

The powdering process may be performed in accordance with the steps illustrated in FIG. 3 and the apparatus used to this end, may be identical, similar or different to the system of FIG. 6A-6B hereinbelow.

In alternative embodiments, the powdering step is replaced with a coating step, in which the laminated device is coated with a liquid or other material.

In a second optional (albeit preferable) quality control step 170, the powdered laminated device 162 is visually inspected to check the quality of the powdered surface thereof. If the device 162 does not meet the required quality, it is rejected in stream 176. If it meets the required quality, an "accepted" powdered laminated device 172 is passed to a folding step 180.

Figure 7A:
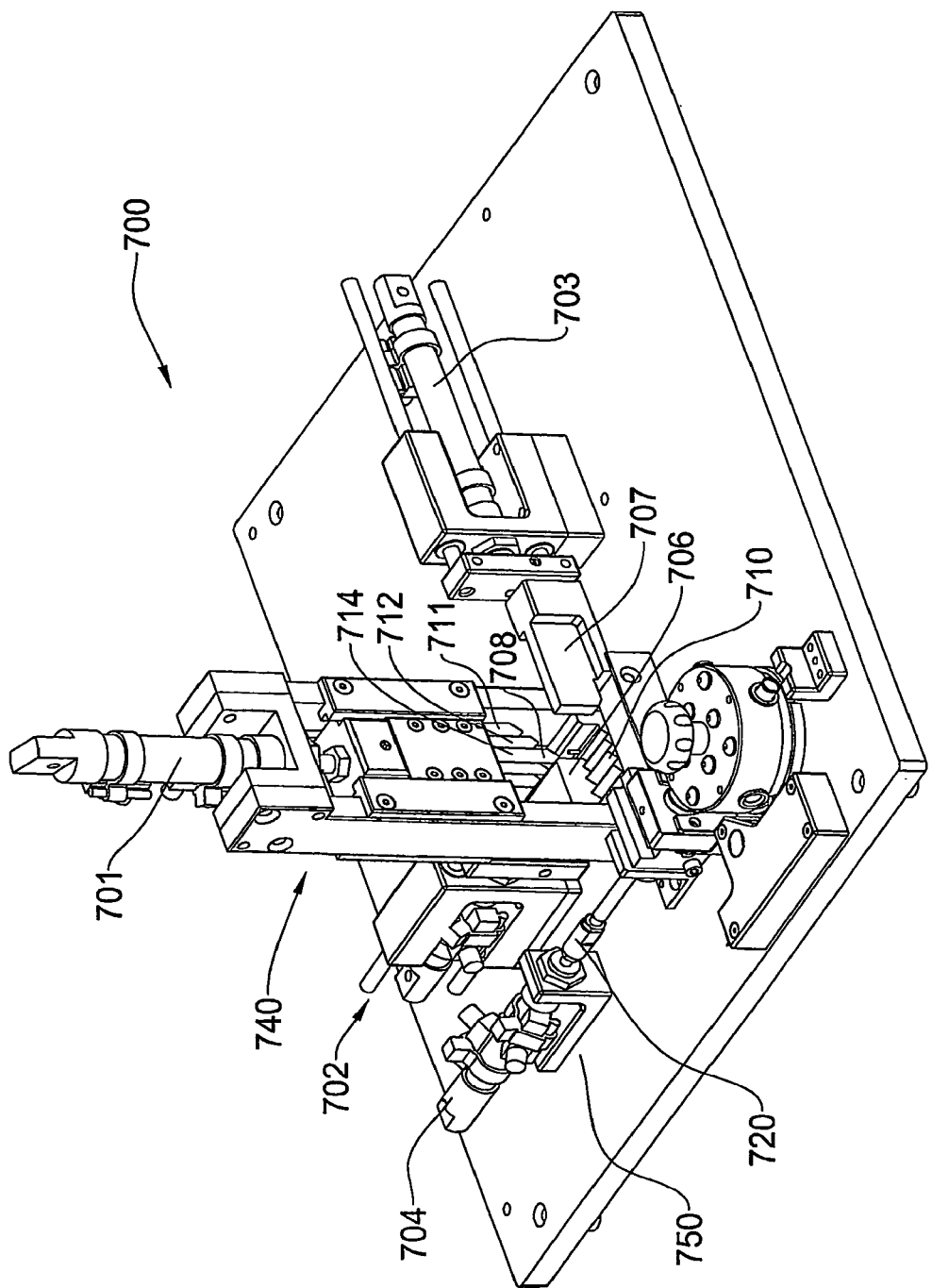
FIG. 7A is a simplified perspective view of an apparatus for folding a device, in accordance with a preferred embodiment of the present invention.
Figure 7B:
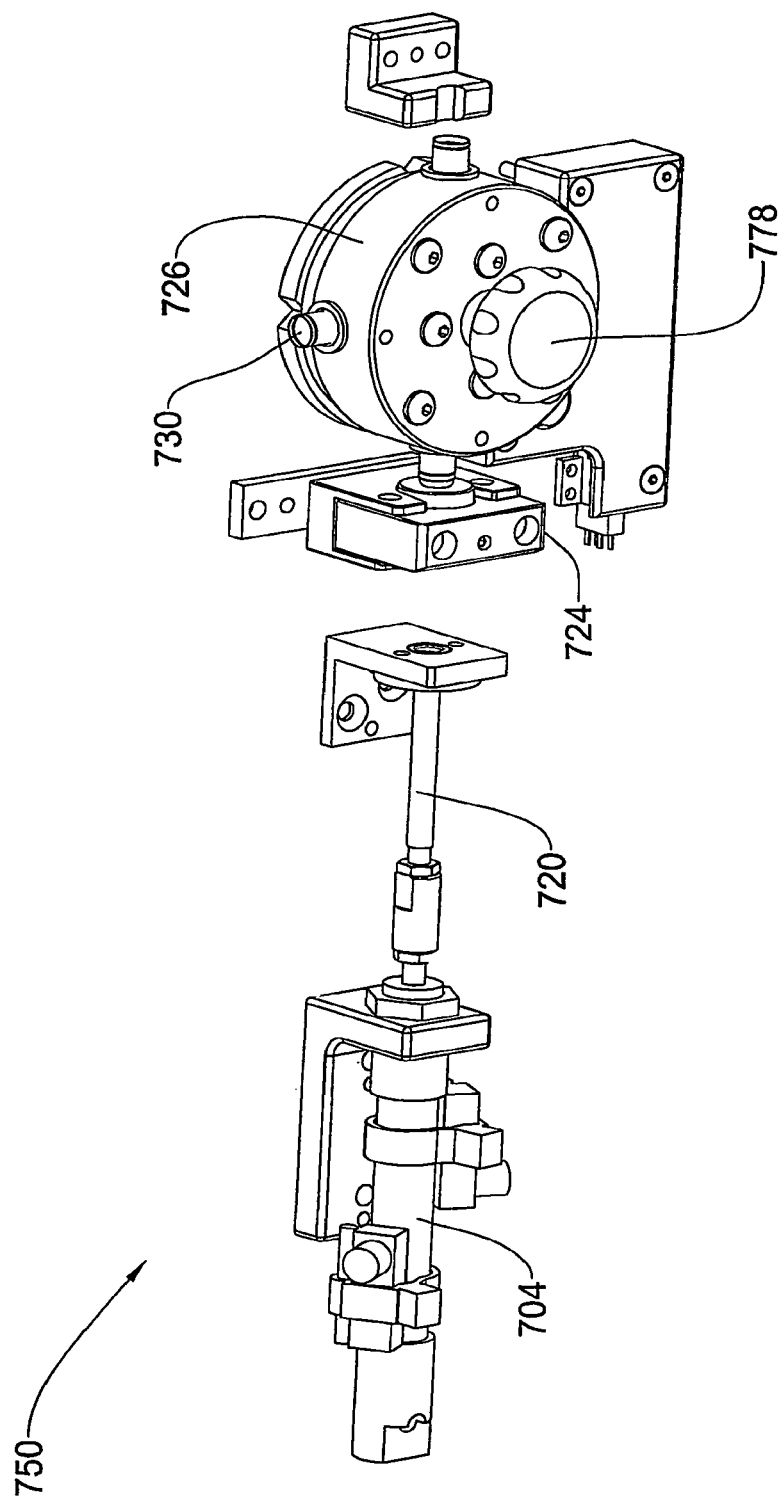
FIG. 7B is a simplified perspective view of an apparatus for inserting a folded device in to a capsule, in accordance with a preferred embodiment of the present invention.
Figure 8:
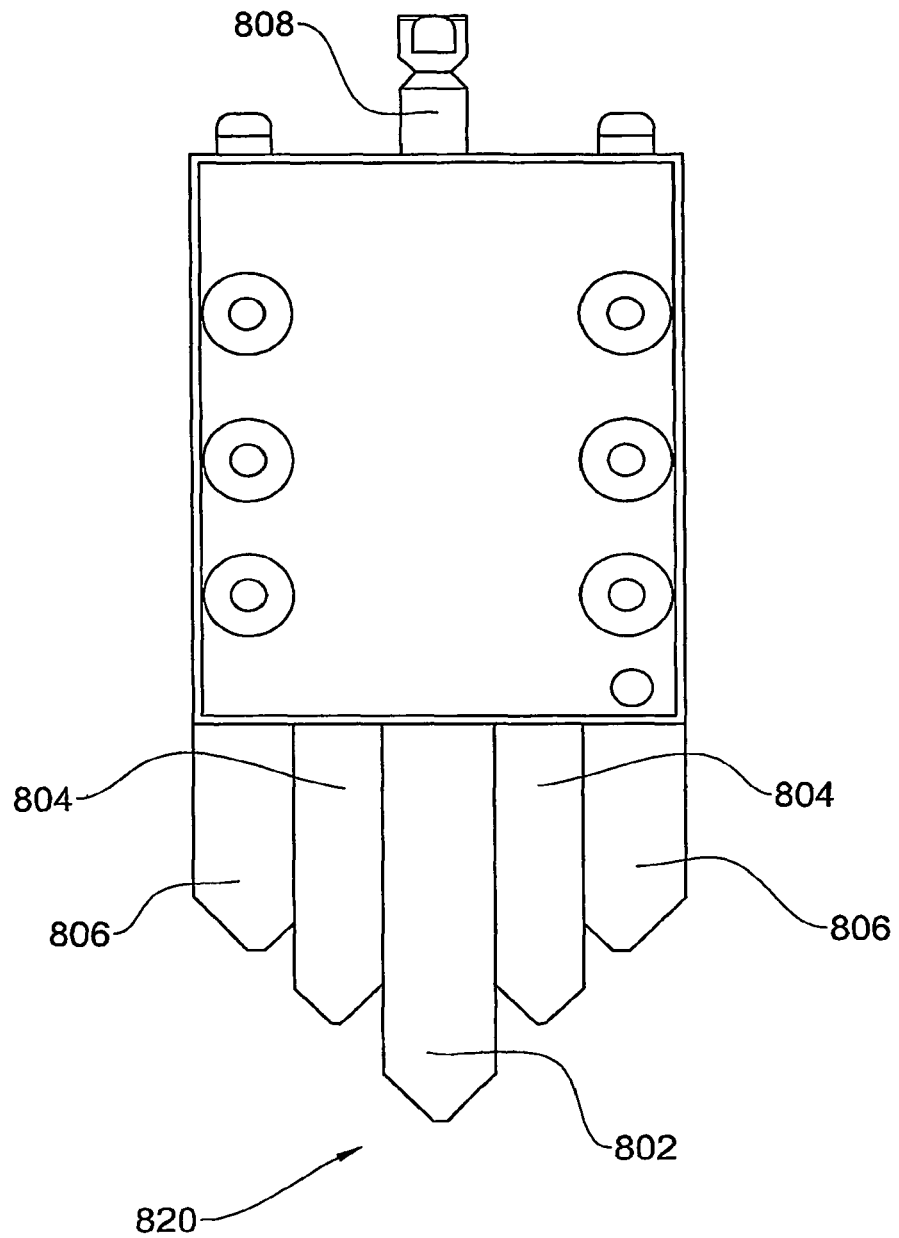
FIG. 8 is a simplified side view of an upper face of a press forming part of an apparatus for folding an integrated device in accordance with a preferred embodiment of the invention.
Figure 9:
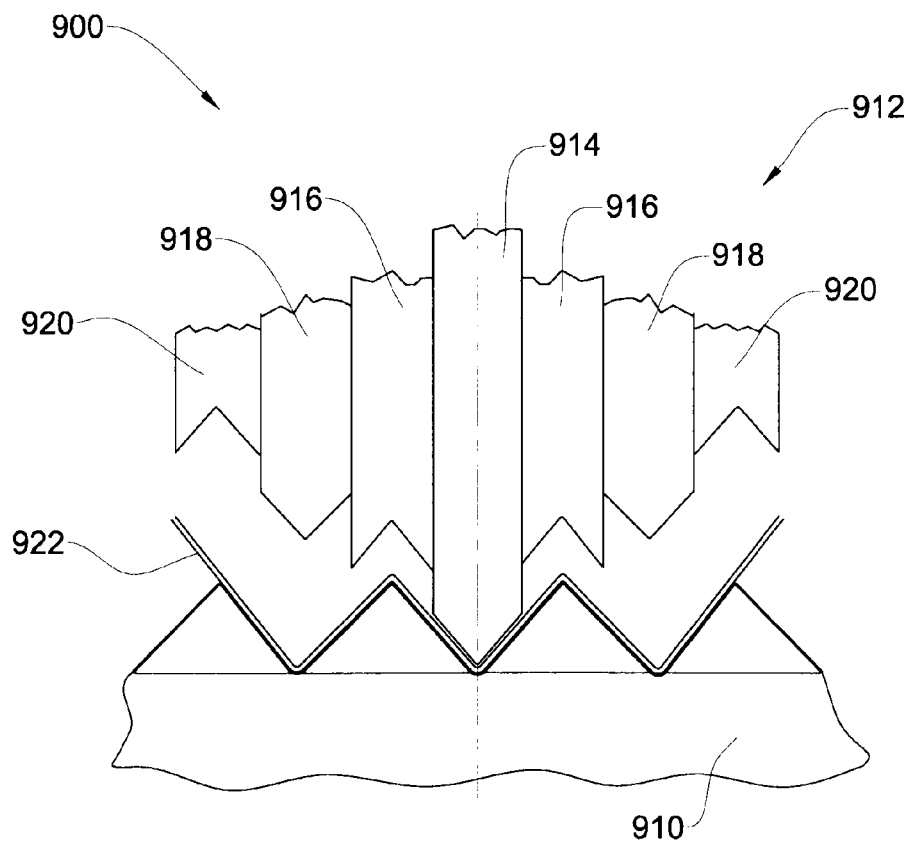
FIG. 9 is a simplified side view of two faces of a press while sandwiching a laminated device in accordance with another preferred embodiment of the invention.

In folding (bending) step 180, device 172, which is essentially planar, is placed in a folding apparatus, such as, but not limited to, the apparatuses of FIGS. 7 to 9.

In accordance with one preferred embodiment, laminated device 172 has dimensions of height/width/thickness 45×(18 to 24)×0.7 mm. Upon completing the folding process 180, the resulting folded device 182 has dimensions 7.3×(18 to 24)× 7.7 mm. In accordance with this embodiment, the projected surface:volume ratio of the laminated device 172 are 1.25 mm$^{-1}$, whereas after folding, the projected surface to volume ratio are 0.0161 mm$^{-1}$.

In folding step 180, laminated device 172 is preferably folded into an accordion-like shape. This folding step 180 normally comprises inserting the device into a press having two corrugated faces. Specifically, the laminated device 172 which is substantially two-dimensional is mounted onto a bending base having a corrugated surface; and pressed by a block having ridges corresponding to said corrugated surface so as to form a folded device 182 having an undulating three-dimensional surface, wherein the undulations thereof correspond to the shape of the corrugated surface.

Additionally or alternatively, laminated device 172 may be manipulated to further reduce its projected surface area by e.g. folding, bending, twisting, wrapping, winding, rolling or crimping in the same or another dimension of the undulated three dimensional device 182.

In accordance with one embodiment, the folding step 180 may comprise a number of manipulations on the unfolded laminated device 172. For example, the folded device following pressing in the folding apparatus may be further squeezed by applying a force perpendicular to a third dimension of the undulating three-dimensional device to the two ends thereof so as to reduce the projected surface area of the resultant folded device 182. This additional squeezing is at times an integral part of the encapsulation step 190 so as to facilitate the insertion of the folded device into the enclosure (e.g. a capsule).

In encapsulated step 190, folded device 182 is then encapsulated inside a capsule 184. Step 190 may, for example, comprise placing (typically by squeezing) the folded device into a capsule base and then fitting a capsule cap onto the capsule base so as to form a encapsulated folded delivery system 192. As appreciated by those versed in the art, other encapsulation process may be applied instead of the above encapsulation step 190.

In accordance with one preferred embodiment, capsule 184 is made of gelatin, however, any alternative pharmaceutically acceptable materials known in the art may be used. The capsule may be of any suitable geometry to house folded device 182. In accordance with one embodiment of the invention, the dimensions of capsule 184 are: internal: diameter of 7.8 mm, length 23-25 mm; external diameter 8.15 mm, length 23.3-25.3 mm. Capsules may be obtained commercially from Capsugel, (NJ, USA). It is noted that the above dimensions are provided for illustration only and should not be construed as limiting the invention. Any other type of capsule and any other dimensions are as well applicable. Preferably, the capsule (or any other enclosure) is selected so as to facilitate oral intake of the folded delivery system.

In some embodiments, encapsulation step 190 is replaced with an enclosing step in which the device 182 is enclosed by some other suitable enclosure means known in the art.

In a third optional quality control step 195, encapsulated folded delivery device 192 is visually inspected for faults. If any significant fault or defect is found, device 192 is rejected into a reject stream 196. If device 192 passes the quality control inspection and is considered as approved device 198, it is passed to a packaging step 197.

Typically in packaging step 197, a number of encapsulated delivery devices 198 are packed together in a suitable packaging 194 to provide a package 199 of deliver devices. Preferably, the encapsulated delivery devices 198 are packed in blister packages as are known in the art. A non-limiting example of a blister package is that commercially available from O. M. A. R. (Italy). It is noted that the packaging may be performed automatically, by the use of automated machines such as Fantasy Plus or others as known in the art.

The packaged delivery device may then be further labelled appropriately and packed into boxes or cartons, ready for marketing and/or storage and/or shipping.

In other preferred embodiments, the delivery device 198 are not packed into blisters but rather into packed into bottles, jars, packets, boxes or other dispensing means known in the art.

The resultant packages 199 are then ready for use including storage, transportation and marketing.

Reference is now made to FIG. 2, which is a simplified flowchart 200 illustrating further details of dicing step 110 step of FIG. 1A.

In a first step, referred to as the removing borders step 210, a sheet of material 202, is cut and its borders 206 are removed so as to form at least one essentially rectangular or oval planar large segment 212 of the sheet. It is noted that this step is optional and is typically required in cases where the large sheet has defects (e.g. bents or other irregularities) in their perimeter.

In a cutting step 220, the large segment 212 is cut into several pieces of at least one shape 222, such as a square, rectangle, trapezoid, oval, circle as well as other polygonal shape (which may be skewed or truncated at one or more of their corners). In accordance with one preferred embodiment, the shape of the sheets is a rectangle truncated at its four corners (at times with curved sides). Remnants materials 226 are removed from the shapes 222, 224 and 228. In some embodiments the sheets 222, 224 and 228 are cut into quarters at this stage. Steps 210, 220 may be performed on several different materials in series or in parallel or in a combination thereof. For example, sheet 202 may represent a first, typically polymeric, material that when wetted is permeable to the active agent and is cut into shape 222, sheet 204 may represent second typically polymeric, material that has a mechanical strength such that when the device is wetted and unfolding, the second polymeric material facilitates retention of the unfolded device in an essentially planar configuration, and is cut into shape 224, and sheet 208 may represent a third, typically polymeric material, or may be non-polymeric and is cut into shape 228. The sheet 208 is adapted to contain or house one or more active agents. In some cases the agent is embedded in sheet 208. In other cases, the agent may be retained/bound either physically or chemically to the sheet 208. In yet other embodiments, the agent may be entrapped between at least two layers of the sheet. The above characteristics of the sheets 202, 204 and 208 may be achieved by the selection of one or a combination of polymers which are soluble or insoluble in gastric content as detailed hereinabove. It is noted that while preferably sheets 202, 204 and 208 have different properties upon wetting, i.e. to provide a delivery device with several layers originating from different sheets; it is also possible that all layers of the resulting device be derived from the same sheet.

In one preferred embodiment, once all the required shaped pieces 222, 224 and 228 have been cut in step 220, they are oriented either manually or automatically or in combination thereof in an orientation step 230. This orientation step may involve two-dimensional and or three-dimensional orientation on a reference surface, such as a cutting board. Oriented pieces 232, 234 and 238 are then mounted into a dicing apparatus forming part of assembling step 240. Assembled mounted pieces 242, 244 and 248 are then diced to shape in dicing step 250. The dicing step may dice pieces 242, 244 and 248 in series or in parallel, in one or more orientation, using one or more dicing blades. The diced shaped pieces 252, 254 and 258 are then transferred to either a spraying step such as in step 120 or directly to an assembling step, such as assembling step 130 in FIG. 1B. Alternatively, the spraying step and the assembling step may be integrated as described with respect to FIG. 1B.

In one embodiment, the shaped pieces 242, 244 and 248 are diced in parallel such that a first and second sheet pieces 242 have, at least in part, similar dimensions with similar outer boundaries (so as to form the layers which are referred to herein, at times, by the term "external layers"); the second sheet pieces form 244 is in the shape of frame(s), suitable for mounting on one of the first sheet pieces and for housing the third sheet piece therein (piece 248, typically, the agent-carrying layer). In an alternative embodiment, a first and second sheet pieces 242 have at least in part, similar dimensions however, with a different outline of the outer boundaries.

Figure 3:
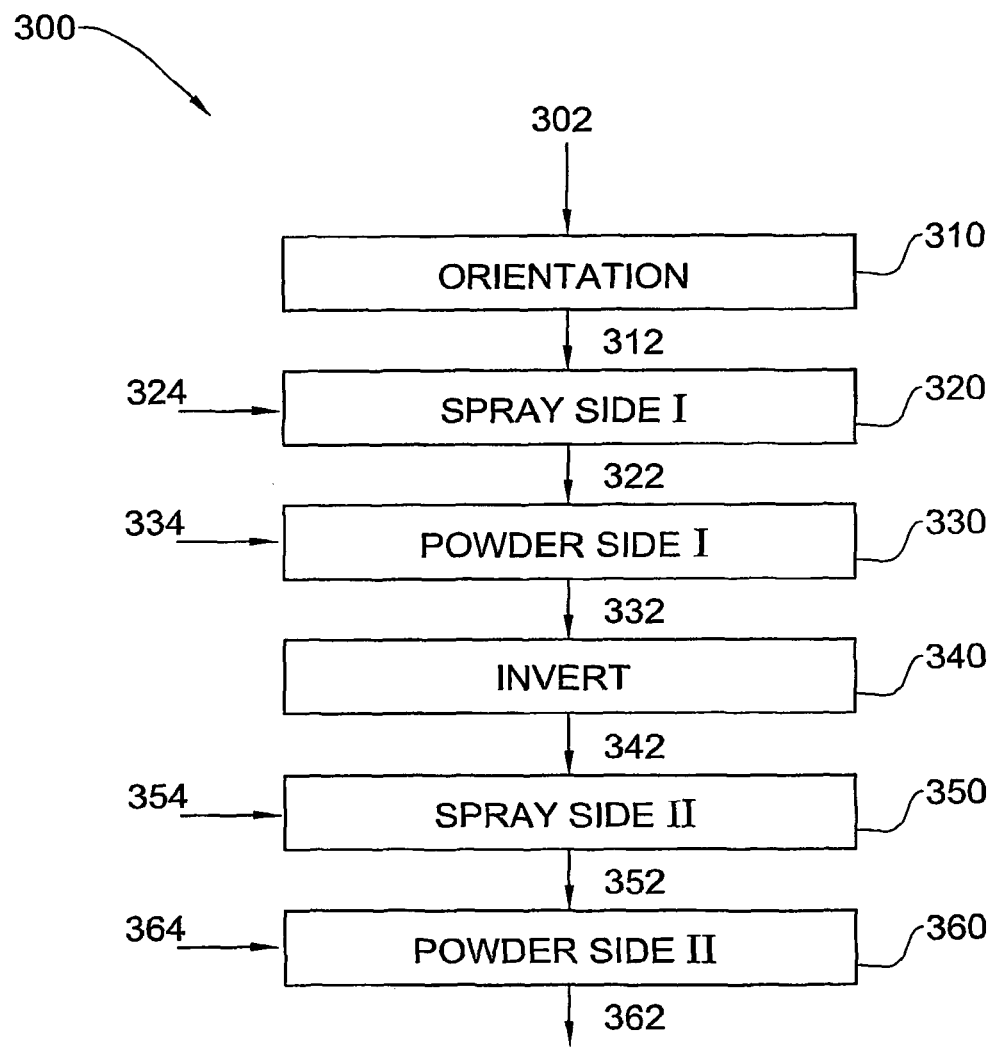
FIG. 3 is a simplified flowchart illustrating details of a powdering step of FIG. 1B.

Reference is now made to FIG. 3, which is a simplified flowchart, 300 illustrating further details of a powdering 160 step of FIG. 1B.

In an orientation step 310, one or more laminated devices 302 are orientated to lie horizontally. The devices 302 may be similar to, identical to or different from device 152 of FIG. 1B. According to one embodiment, the different laminated devices 302 may be oriented as shown in sliding board 611 shown in FIG. 6B.

In a preferred embodiment, laminated device 302 comprises a lower external layer of first sheet, upon which a perimeter frame of second sheet from a second material is mounted. Inside the frame are one or more pieces of the third sheet containing at least one active agent. Mounted on the frame, so as to cover the one or more pieces of the third sheet is another piece of the first sheet, as further illustrated in FIG. 4 hereinbelow.

In a first spraying step 320, the orientated devices 312 are sprayed on one face of the laminated device 312 (e.g. the upper face of the laminated device) with ethanol 324 (according to one embodiment, with 2 mg per spray pulse) or any other suitable organic solvent to provide a sticky upper-faced device 322.

Thereafter, in a first powdering step 330, form 322 is powdered with powder 334 so as to form a non-sticky upper-faced device 332. Powder 334 is typically an anti-adhering powder such as that described in connection with step 160 in FIG. 1B. In accordance with one embodiment, a layer of 0.05 mm thickness or 0.03-0.07 g/laminated dosage form of powder is sprayed on device 322 to form the non-sticky upper-faced device 332.

In an inverting step 340, device 332 is inverted about a horizontal axis, such that the non-sticky face is now face-down. It is noted that the inverting step may be performed by an automated machine, e.g. a robot, or manually.

In a second spraying step 350, a face-down device 342 is sprayed with ethanol 354 to form a sticky lower faced device 352. This step is substantially similar to step 320.

In a second powdering step 360 the sticky lower faced device 352, is powdered with an anti-adhering powder 364 (which is typically the same anti-adhering powder applied to the upper face 332) to form a two-sided anti adhering device 362. Device 362 may be similar or identical to the dosage forms disclosed in FIGS. 1-3 of U.S. Pat. No. 6,685,962 to Friedman et al. incorporated herein by reference in its entirety.

It should be understood that though the flowcharts herein may refer to one delivery devices, they are not limited thereto. The methods and apparatuses of the present invention are designed to produce a large number of delivery devices and are preferably designed to mass produce such delivery devices.

Reference is now made to FIG. 4, which is a schematic illustration of the main steps of the method of FIG. 1B.

In a first assembling step, 410, parallel to step 130 of FIG. 1B, sheet shapes 422, 423, 424 and 426 (corresponding to portions 122, 123, 124 and 126 in FIG. 1B) are assembled. Typically, shape 424 is assembled on shape 422 and thereafter, shape 426 containing the active agent is inserted into shape 424 thereby placed on shape 422. Thus, shapes 424 and 426 form a second layer on first layer 422. Shape 424 is sometimes referred to as a frame and the combination of the frame with the agent carrying layer 426 is sometimes referred to as the functional layer. In some embodiments, a third layer is formed by assembling shape 423 on the second layer so as to form a laminated device 432. Many possible variations of step 410 are envisaged, and the invention should not be narrowly construed as limited to the embodiments disclosed in the specification and figures.

In a folding step 420, the multi-layer laminated device 432 is first typically pressed in a press machine such as, but not limited to that illustrated in the folding apparatus 700 of FIG. 7, comprising upper bend tool 900 of FIG. 8 and bending base 1102 of FIG. 9.

An essentially planar laminated device 432 is placed on a bending base 442 below an upper bend tool 444. The upper bend tool 444 is then pressed down onto laminated device 432 and forces the laminated device into a folded or bent device 446, similar or identical to device 182 of FIG. 1B.

In a second part of folding step 420, folded device 446 is pressed from the sides to squeeze the folds together to form a compacted folded laminated device 482, similar, dissimilar or identical to device 182 of FIG. 1B. In some cases, device 446 is pushed about a third axis so as to form the folded laminated device 482 in dimensions suitable for insertion into an enclosure.

The folded device 482 is then enclosed in an enclosing step 430, which may be similar, dissimilar or identical to encapsulation step 190 of FIG. 1B. In accordance with this particular embodiment, folded device 482 is inserted into a capsule 484 by first pushing the compacted folded device 482 into a capsule base 486 and fitting onto the capsule base the capsule cap 488 (the second half of the capsule) to form encapsulated device 492. It should be understood that many variations for enclosing device 484 are envisaged for this enclosing step and the invention should not be narrowly construed as limited to the embodiments disclosed in the specification and figures.

In a packaging step 440, encapsulated devices 492 are packaged in suitable packaging 494, similar, dissimilar or identical to packaging 194 of FIG. 1B and the resultant packaged devices are ready for further processing including storage, sale or further packaging. In accordance with one embodiment, packaging may be obtained by any technique known for the preparation of blister packages (not shown). Imprinted cut blister packages may then be inspected in an optional quality control step (not shown) and any rejected packages may be discarded while accepted blister packages may be then packed in boxes for storage, shipping or selling etc. (not shown)

Figure 5:
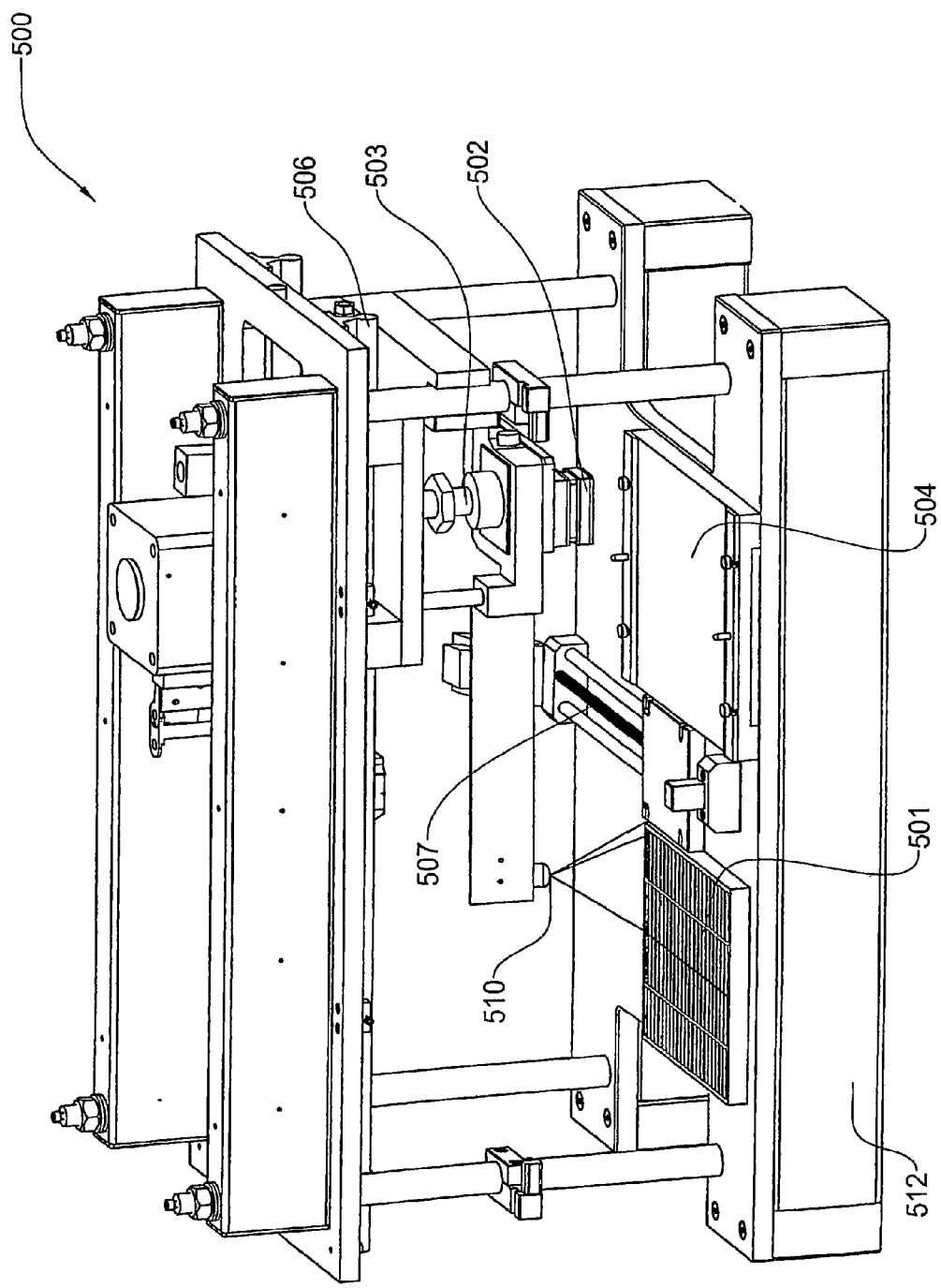
FIG. 5 is a simplified perspective view of an apparatus for dicing and assembling layers into an integrated device in accordance with a preferred embodiment of the present invention.

Turning now to FIG. 5, a simplified perspective view of an apparatus 500 for dicing and assembling a laminated device can be seen, in accordance with a preferred embodiment of the present invention.

As can be seen in FIG. 5, apparatus 500, comprises an assembly plate 501, a cutting tool 502, a piston 503, a cutting board 504, an X slider 506, a Y slider 507 at least one support 512. The apparatus is preferably at least in part automatically controlled and is operative to move sliced pieces from the sheet of material onto the assembly plate 501 by means of sliders 506 and 507. Once actuated, cutting tool 502 is operative to cut the sheet of material on board 504 into the sliced pieces, the pieces being of a predetermined shape so as to form pieces 112, 113, 116 and 118 as in FIG. 1B. Once on the assembly plate 501 each sliced piece is sprayed by a spray nozzle 510. In accordance with one embodiment, a layer of a plurality of sliced pieces are placed on assembly plate 501 and simultaneously sprayed with an adhering substance as described above. Thereafter, a second layer of a plurality of pieces, typically of a second material, are mounted on the first layer of sliced pieces and sprayed. In accordance with one embodiment, this layer of a second material forms the frame into which the pieces carrying the agent are individually inserted to form a second layer which is also sprayed. This sprayed second layer is covered by a third layer. The construction of the layers is also illustrated hereinbelow with respect to FIG. 4.

Figure 6A:
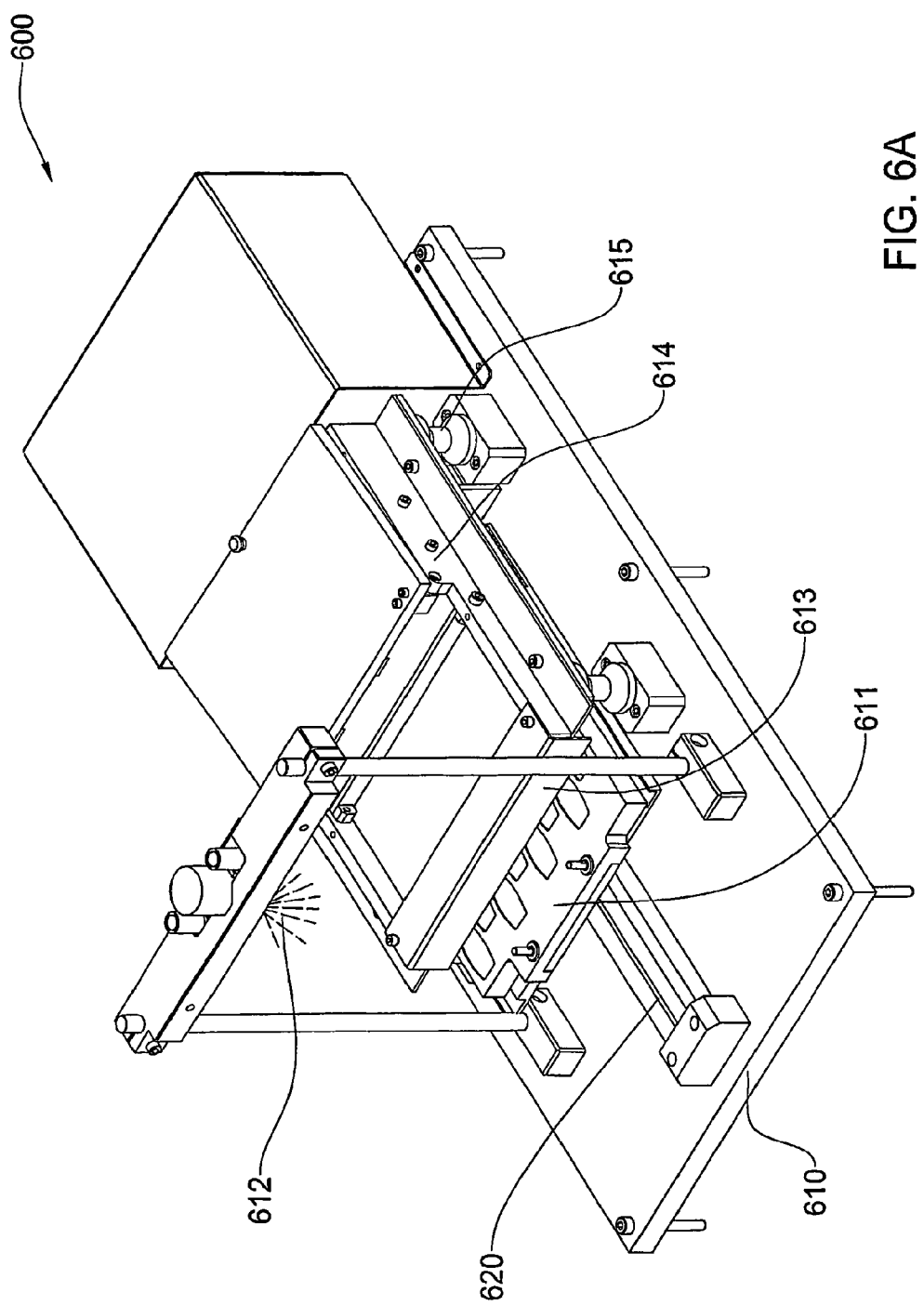
FIG. 6A is a simplified perspective view of an apparatus for powdering an integrated device in accordance with a preferred embodiment of the present invention.

FIG. 6A is simplified perspective view of an apparatus 600 for powdering and spraying a laminated device such as 152 in FIG. 1B, in accordance with a preferred embodiment of the present invention. Apparatus 600 comprises a base plate 610, carrying a slide board 611 upon which the devices 312 or 432 may be placed. The sliding board is movable along a slide lead screw 620 for so as to locate the sliding board with the devices thereon in position for spraying and powdering. The devices may be sprayed on one or more sides with an agent such as ethanol by means of a spraying system 612 so as to form sprayed devices 322. Thereafter, the devices 322, may be coated or powered by coating dispersion system 613 so as to produce coated devices 162, 332. The coated devices may then be inverted (manually or automatically) and the spraying and coating procedure may be repeated to form powdered devices 162 and 362. Apparatus 600 comprises a powder cartridge 614 a vibrating system 615 for facilitating powdering of the sprayed devices 322 and 352 by the vibration of cartridge 614.

In one embodiment, the laminated devices 432 are moved mechanically by system 600 onto the base plate 611, is sprayed with ethanol by system 612 on one side thereof and is moved back by system 600 to the its point of origin. Thereafter, the vibrating system 615 is activated and coats the device with a powder, for example. The device is then moved by system 600 in the direction of the dispersion system 613 and the coated sprayed device is moved mechanically to it point of origin in system 600.

Figure 6B:
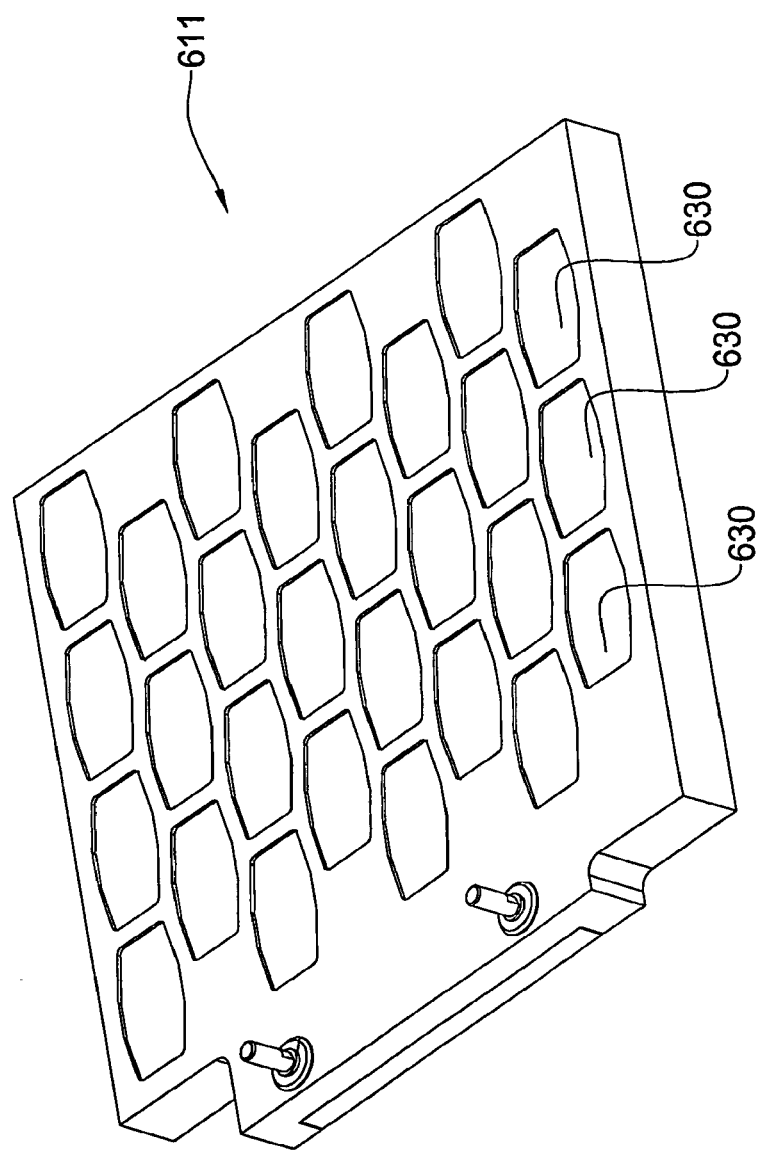
FIG. 6B is a simplified perspective view of a sliding board forming part of the system for powdering of FIG. 6A.

FIG. 6B is a perspective view of slide board 611 showing a plurality of oriented laminated devices 630 arranged thereon for handling in apparatus 600.

Reference is now made to FIG. 7A, which is a simplified perspective view of an apparatus 700 for folding a laminated device, in accordance with a preferred embodiment of the present invention. Folding apparatus 700 comprises a folding press 740 comprising two faces, an upper bend tool 708 and a bending base 710, each having a corrugated surface; the folding apparatus also comprises a number of pistons 701 (for moving downwardly and upwardly upper bend tool 708), 702 (for moving folded device 446 away from bending base 710 by pushing push block 706), 703 (for further squeezing folded device 446 to obtain device 482 in FIG. 4), and 704 (for pushing folded device 482 into the capsule base 486); a push block 706, a side slide block 707, an upper bend tool 708, and bending base 710, and a number of fingers 711, 712 and 714. Further shown in FIG. 7A is the encapsulating apparatus 750 which is discussed in more detail in FIG. 7B.

Firstly, a laminated device 432 is placed onto bending base 710 and upper bend tool 708 is automatically lowered towards bending base 710 carrying the laminated device 432 thereby applying pressure onto the device so as to form folded device 446. Thereafter, push block 706 pushes and thereby releases the folded device such as 446 (FIG. 4), from the bending base 710. Thereafter, side slide block 707 presses the device 446 into a pressed device, such as 482 in FIG. 4. Subsequently, a mechanical bar 720 pushes device 482 into a capsule base 486 so as to form an encapsulated dosage form 492 (FIG. 4).

In FIG. 7B, further details of an encapsulating apparatus 750 generally shown in FIG. 7A are illustrated. Specifically shown are a piston 704, an encapsulation pin 720, a squeezing hole 724, a capsule base holder 730 on a capsule base revolver 726 carrying a plurality of capsule base holder 730 and a rotation axis 778. In operation, a folded device 482 is pushed by side slide block 707 in between encapsulation pin 720 and a squeezing hole 724. Piston 704 then activates encapsulation pin 720 to push the folded device through squeezing hole 724 and thereafter into a capsule base located in the capsule base holder 730. Once introduced into a capsule base, rotation axis 778 rotates the capsule base revolver 726 so as to position the following capsule base holder in position for encapsulating the next folded device. The capsule cap may then be fitted onto the capsule base manually or automatically (not shown).

FIG. 8 shows further details of an upper bend tool such as 708 of FIG. 7A. In this specific, non-limiting example, an upper bend tool 800 is shown comprising a plurality of bending fingers, including, a center finger 802, a pair of second fingers 804, and a pair of outer fingers 806 and connection pin 808. The plurality of fingers provide the upper bend tool with a corrugated surface. Each finger is independently movable downwardly by the actuation of connecting pin 808. As shown in this specific embodiment, the corrugated surface is formed a central finger 802 having a first length, and a pair of secondary movable fingers 804 siding said central finger 802 and having a second length being shorter than the first length, and a third pair of fingers 806 having a third length that is shorter than the second length. The corrugated surface is provided by a proximal ends 820 of each finger being vertexed. It is to be noted that other shapes of proximal ends 820 are applicable, such as curved and concaved ends, zigzagged ends, and combinations of same.

FIG. 9 shows a side view of the arrangement of components in a folding press 900 (740 in FIG. 7A) including a bending base tool 910 having an undulating/corrugated surface; a plurality of fingers forming part of an upper bend push 912 and including a central finger 914, a pair of secondary fingers 916, a pair of intermediate fingers 918 and a pair of outer fingers 920. Further shown is undulated/folded device 922. In operation, center finger 914 is forced down onto a device 432, and thereafter in sequence, two secondary fingers 916, two intermediate fingers 918 and two outer fingers 920 thereby forcing device 432 to obtain the shape of the corrugated surface as represented by device 922. The device 922 is then pushed by push block 706 (FIG. 7A) into encapsulating apparatus 750. It is noted that other embodiments of the press apparatus are applicable, such as a press in which other sequences of movement (downwardly and upwardly) of the fingers takes place. For example, the fingers may be activated such that together with the central finger the two siding fingers (secondary fingers) are lowered, followed by the intermediate etc., or all fingers may be pressed downwardly together. Further alternatively, the pressing device may be constructed such the array of movable fingers are located so as to form the base onto which the integrated device is placed and upon operation, press is achieved by moving the finger(s) upwardly towards a respective upper bend tool.

Figure 10:
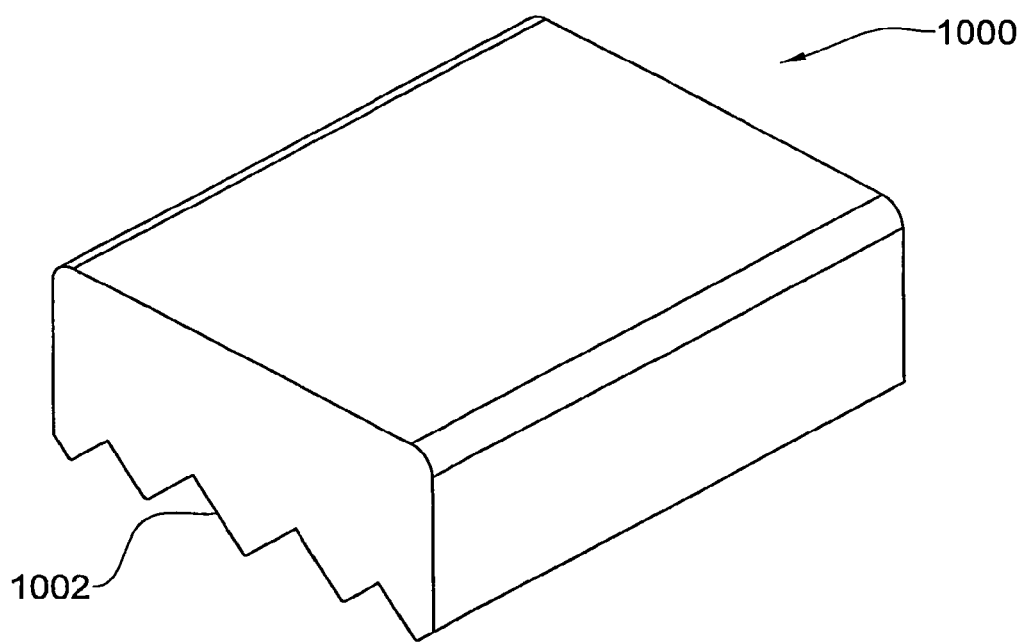
FIG. 10 is a simplified perspective view of a push block integrating between the folding apparatus and encapsulating apparatus, in accordance with a preferred embodiment of the invention.
Figure 11A:
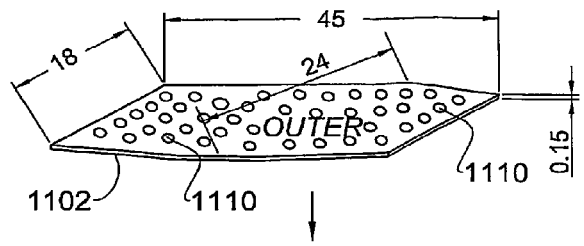
FIG. 11A-11E show a side view of components (FIGS. 12A-12D) of an essentially planar oval delivery device and the integrated device (FIG. 12E) with pores on the two external layers, produced by the method of FIG. 1A, in accordance with a preferred embodiment of the present invention.
Figure 11B:
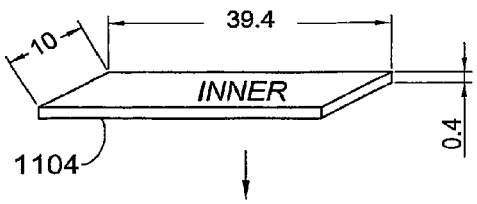
Figure 11C:
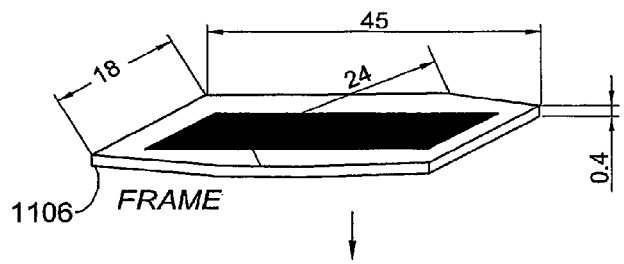
Figure 11D:
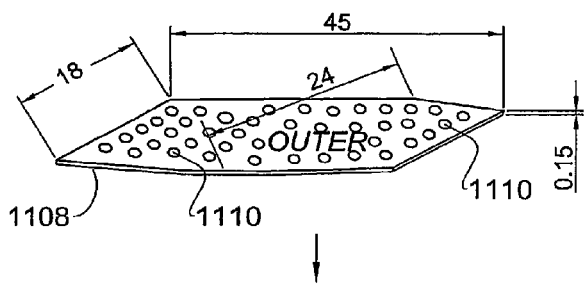
Figure 11E:
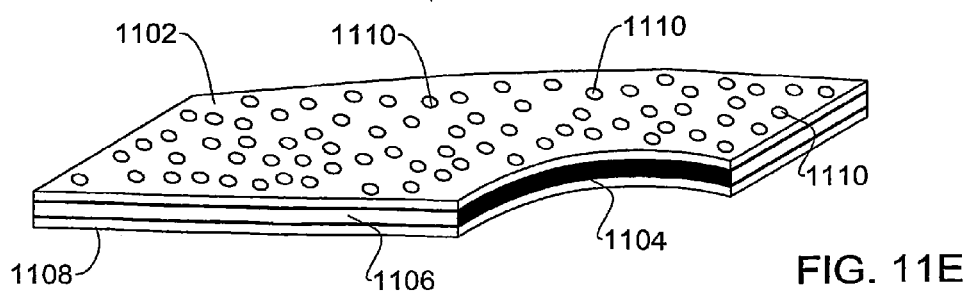
Figure 12A:
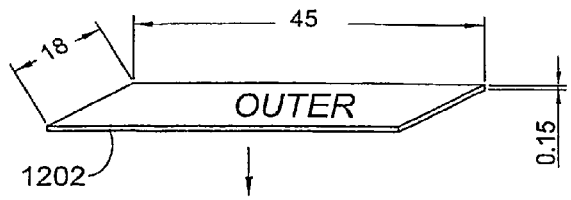
FIG. 12A-12E show a side view of components (FIGS. 13A-13D) of an essentially planar delivery device with the agent being incorporated into separate compartments (FIG. 13B) to form the integrated device (FIG. 13E) produced by the method of FIG. 1A, in accordance with another preferred embodiment of the present invention.
Figure 12B:
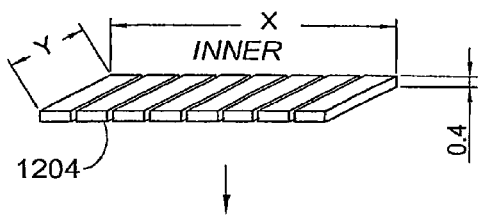
Figure 12C:
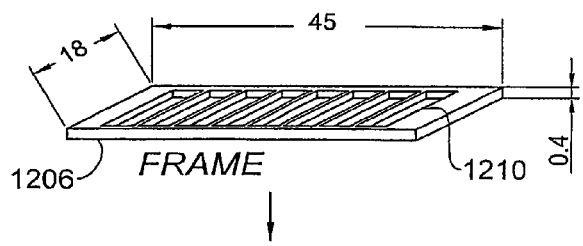
Figure 12D:
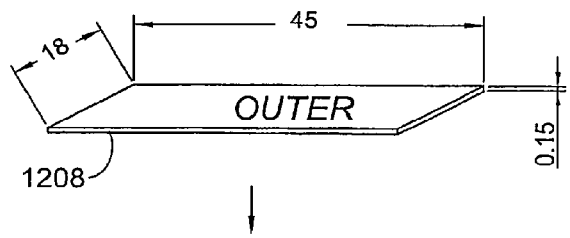
Figure 12E:
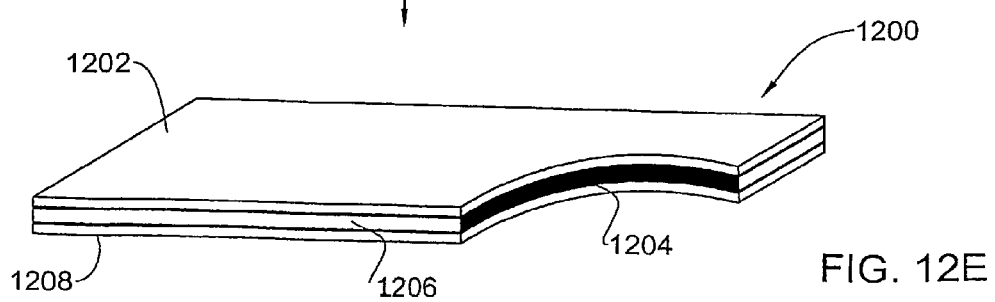

FIG. 10 shows a perspective view of a push block 1000 corresponding to push block 706 of FIG. 7A. Typically, the push block 1000 has a corrugated surface 1002 which matches the corrugated surface of the bending base 710 of FIG. 7A.

Reference is now made to FIG. 11A-11E, which shows a perspective side view of an essentially planar delivery device 1100 and the different components of the device 1102, 1104, 1106, and 1108, in accordance with another preferred embodiment of the invention. According to this specific embodiment, the device 1100 is constructed from two external layers 1102 and 1108 having a plurality of perforations 1110 and sandwiching a frame 1106 hosing an internal matrix 1104 carrying the agent. While layers 1102 and 1108 may be formed of the same or of different materials and may have the same or different thickness, it is preferable that layers 1102 and 1108 are formed of the same polymeric material and have substantially similar thicknesses. Most preferably layers 1102 and 1108 are made of sheet material 104 of FIG. 1B. Preferably, frame 1106 is made of material 108 of FIG. 1B. The frame may comprise one or more layers of polymer. The frame may be continuous or discontinuous. Inner layer preferably comprises material 109 comprising the agent 102, as exemplified in FIG. 1B.

Reference is now made to FIG. 12A-12E, which shows perspective side view of an essentially planar device 1200 also produced by the method of FIG. 1B, in accordance with another preferred embodiment of the present invention. As shown, external layers 1202 and 1208 are sealed (to become permeable to the agent only upon wetting) and enclose a frame 1206 housing an array of compartments 1210 construed from segments 1206 each compartment carrying an agent-releasing formulation in separate segments 1204. The dimensions, provided in the figure in millimeters, should be construed to be illustrative but not limiting. In accordance with this specific embodiment, device 1200 comprises two outer layers, upper outer layer 1202 and lower outer layer 1208. A frame 1206 is mounted on lower layer 1208 and inner layer segments 1204 are inserted into the frame 1206. The upper layer 1202 is then mounted onto the frame 1206 and onto inner segments 1204.

Figure 13A:
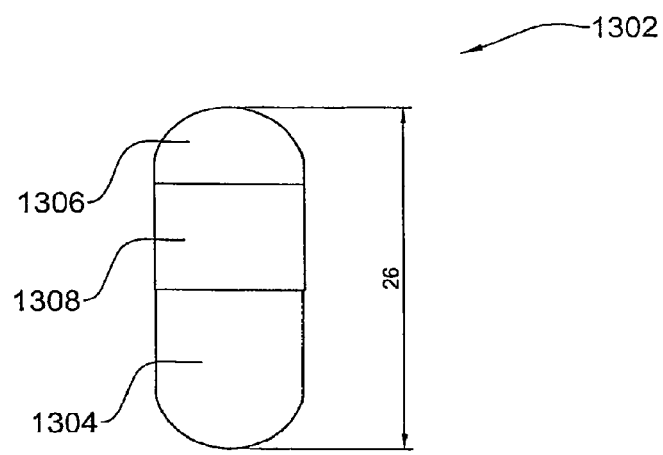
FIG. 13A-13B shows a side and cross-sectional view of an encapsulated folded delivery device produced by the method of FIG. 1A, in accordance with a preferred embodiment of the present invention.
Figure 13B:
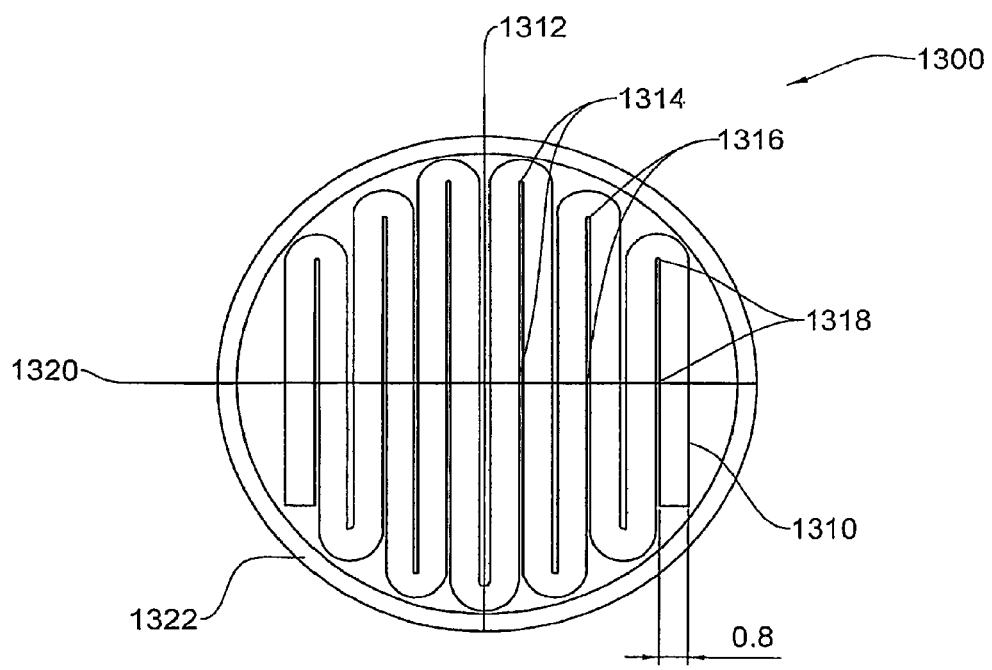

FIG. 13A-13B show, respectively a side view and cross-sectional view of an encapsulated folded device 1300 produced by the method of FIG. 1B, in accordance with a preferred embodiment of the present invention. Encapsulated delivery device comprises a capsule 1302 comprising a capsule base 1304 and a cap 1306, wherein the cap is vertically mountable to form an overlapping region 1308 in close-fit association with the capsule base.

A folded device 1310 placed in capsule 1302 may be similar or identical to dosage form 182 of FIG. 1B. Typically, folding is such so that the projection of the folded device has an area of less than 50%, preferably less than 30% and at times even less than 20% of the unfolded device 172. The dimensions, provided in the figure in millimeters, should be construed to be illustrative but not limiting.

In some embodiments, the folded device, is typically folded parallel to the width of the unfolded device and designed to have folds which are symmetric mirror images about a first axis 1312 and having folds of increasingly smaller amplitudes 1314, 1316, 1318 upon extending away from the first axis, such that upon inducing a force from two ends of a second axis 1320 perpendicular to the first axis, the folded device is pressed to attain an at least partially circular cross-section 1322 for easy insertion into capsule 1302.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination.

Although the invention has been described in conjunction with specific embodiments thereof, it is evident that many alternatives, modifications and variations will be apparent to those skilled in the art.

All publications, patents and patent applications mentioned in this specification are herein incorporated in their entirety by reference into the specification.

The invention claimed is:

1. A method for producing an agent delivery device for oral intake comprising:
   assembling one or more layers comprising one or more materials with an agent or an agent-releasing formulation into a generally planar assembly to form an integrated device;
   folding said integrated delivery device to form a folded integrated delivery device defining a first axis, such that the folded device has folds of increasingly smaller amplitudes upon extending away from the first axis so as to form a partially rounded cross section; and
   at least partially enclosing said folded delivery device to a form suitable for oral delivery.

2. The method according to claim 1, comprising at least one layer in the form of a strip attached to at least one of said one or more layers.

3. The method according to claim 1, wherein said assembling comprises integration of said one or more layers to form a laminated device.

4. The method according to claim 1, comprising assembling two external layers made of a first material and sandwiching a functional layer, the functional layer comprising at least one layer in a form of a strip or plurality of strips made of a second material and comprising the agent or agent-releasing formulation.

5. The method according to claim 1, comprising assembling at least one layer of an enforcing polymeric composition having a mechanical strength such that upon unfolding of the delivery device, the enforcing polymeric composition enables retention of the device in an essentially unfolded configuration.

6. The method according to claim 1, wherein said integrated device comprises two or more layers, and said assembling comprises one or more of:
   one or more of adhering, welding, curing or fusing said two or more layers so as to allow integration between the same; and
   applying an integration agent to said two or more layers so as to facilitate integration between the layers.

7. The method according to claim 1, wherein said assembling comprises at least one of the following:
   embedding said agent or agent releasing formulation into one or more layers;
   trapping said agent or agent releasing formulation within at least two layers;
   enveloping said agent or agent-releasing formulation within at least one polymeric membrane segment; and
   attaching said agent or agent-releasing formulation to or in at least one of said one or more layers of the device, nano- or microparticles, powder, liquid or compressed solids or a matrix.

8. The method according to claim 7, comprising assembling a laminated device comprising two external layers made of a first material and sandwiching one or more layers comprising one or more strips made of a second material and comprising the agent or agent-releasing formulation.

9. The method according to claim 8, wherein at least one of said external layers is perforated or assumes perforations upon wetting.

10. The method according to claim 1, wherein said folding comprises manipulation of said integrated device into a compacted integrated device which is at least five times less in dimension than that of the integrated device prior to said folding.

11. The method according to claim 1, wherein said folding comprises any one of:
   placing said integrated device between two opposite faces of a press, each face having a corrugated surface with ridges of one corrugated surface being essentially opposite to troughs of the other corrugated surface and essentially fitting one into the other; and pressing the two opposite faces one versus the other such that an undulated, three dimensional device is formed with undulations that correspond in shape to that of said corrugated surfaces; and
   placing said integrated device in between two opposite faces of a press, each face having a corrugated surface with ridges of one corrugated surface being essentially opposite to troughs of the other corrugated surface and essentially fitting one into the other; pressing the two opposite faces one versus the other such that an undulated, three dimensional device is formed with undulations that correspond in shape to that of said corrugated surfaces; and
   applying a press so as to push sides of the undulated device in a direction perpendicular to said undulation, into a folded device having folds formed along ridges and troughs of the undulation.

12. The method according to claim 1, for producing a gastro-retentive oral delivery device.

13. An agent delivery device for oral intake, comprising a folded single or multi-layered integrated device comprising an agent or agent releasing formulation, the folded integrated device being at least partially enclosed within or by an enclosure, said agent delivery device being prepared by the method as defined in claim 1.

14. The method according to claim 1, wherein said folding comprises:
   placing said integrated device in between two opposite faces of a press, each face having a corrugated surface with ridges of one corrugated surface being essentially opposite to troughs of the other corrugated surface and essentially fitting one into the other, wherein at least one said corrugated surface is formed by a series of fingers comprising a movable central finger having a first length, and at least one pair of secondary movable fingers siding said central finger and having a second length being shorter than the first length, and controlling upwardly and downwardly movement of said central finger and at least one pair of secondary fingers towards the said other corrugated surface; and
   pressing the two opposite faces one towards the other such said device is formed wherein said folds correspond to said corrugated surfaces.

15. A method for folding a generally planar discrete single or multi-layered sheet comprising:
   folding said generally planar discrete sheet to provide a folded discrete sheet comprising a plurality of adjacent folded segments having respective fold lines extending along a first dimension of said discrete sheet;

said folded discrete sheet providing a folded integrated delivery device defining a first axis, such that the folded device has folds of increasingly smaller amplitudes upon extending away from the first axis so as to form a partially rounded cross section; and pressing said folded segments of said folded discrete sheet towards one another along directions generally orthogonal to said first dimension to provide a compact configuration for the folded sheet.

16. A method according to claim 15, further comprising at least partially enclosing said folded sheet to a form suitable for oral delivery.

17. A method for producing an agent delivery device for oral intake, the method comprising:

providing one or more generally planar layers comprising one or more materials and one or more agent or an agent-releasing formulation;

folding the one or more generally planar layers to form a folded device defining a first axis, such that the folded device has folds of increasingly smaller amplitudes upon extending away from the first axis so as to form an at least partially rounded cross section; and at least partially enclosing the folded device to a form the agent delivery device for oral intake.

* * * * *